US007218386B2

(12) United States Patent
Alcock et al.

(10) Patent No.: US 7,218,386 B2
(45) Date of Patent: May 15, 2007

(54) DETECTION OF PRINTING AND COATING MEDIA

(75) Inventors: Robin Daniel Alcock, Bristol (GB); Jeremy Michael Coupland, West Bridgeford (GB); Neil Aitchison Macnab, London (GB)

(73) Assignee: The Governor & Company of the Bank of England, London (GB)

( * ) Notice: Subject to any disclaimer, the term of this patent is extended or adjusted under 35 U.S.C. 154(b) by 483 days.

(21) Appl. No.: 10/399,055

(22) PCT Filed: Oct. 12, 2001

(86) PCT No.: PCT/GB01/04569

§ 371 (c)(1),
(2), (4) Date: Oct. 23, 2003

(87) PCT Pub. No.: WO02/31780

PCT Pub. Date: Apr. 18, 2002

(65) Prior Publication Data
US 2004/0051862 A1 Mar. 18, 2004

(30) Foreign Application Priority Data
Oct. 13, 2000 (GB) ................................ 0025096.9

(51) Int. Cl.
*G06K 9/74* (2006.01)
(52) U.S. Cl. ....................................................... 356/71
(58) Field of Classification Search ..................... None
See application file for complete search history.

(56) References Cited

U.S. PATENT DOCUMENTS

| 4,514,085 | A | * | 4/1985 | Kaye ............................ 356/71 |
| 4,710,627 | A | * | 12/1987 | Baltes et al. ........... 250/339.11 |
| 4,947,441 | A | * | 8/1990 | Hara et al. ................... 382/135 |
| 6,365,907 | B1 | * | 4/2002 | Staub et al. ................. 250/566 |
| 6,473,165 | B1 | * | 10/2002 | Coombs et al. ............... 356/71 |

* cited by examiner

*Primary Examiner*—Michael P. Stafira
(74) *Attorney, Agent, or Firm*—Barnes & Thornburg LLP

(57) ABSTRACT

Method and apparatus are described for determining if an optically variable material (OVM) is present in or on a surface, typically of a security document such as a banknote. In some embodiments the particular type of OVM is identified. In other embodiments a pass or fail signal is generated depending on whether a specific OVM is found on the surface. The surface is subjected to at least two different wavelengths of illuminating light at a particular angle to the surface and the intensity of the light reflected and/or scattered light from the surface is determined using photodiodes. The analogue output from the photodiodes may be digitised and the digital values processed according to one or another of different algorithms described, so as to produce an output signal whose value can be compared with one or more stored reference values in a look-up table, to produce a decision signal. Comparison of the analogue photodiode output signal values against a look-up table can be used to indicate the concentration of the OVM on the surface. Methods and apparatus are described for document authentication and identification, coating quality control and document sorting, by employing the methods and apparatus described.

107 Claims, 18 Drawing Sheets

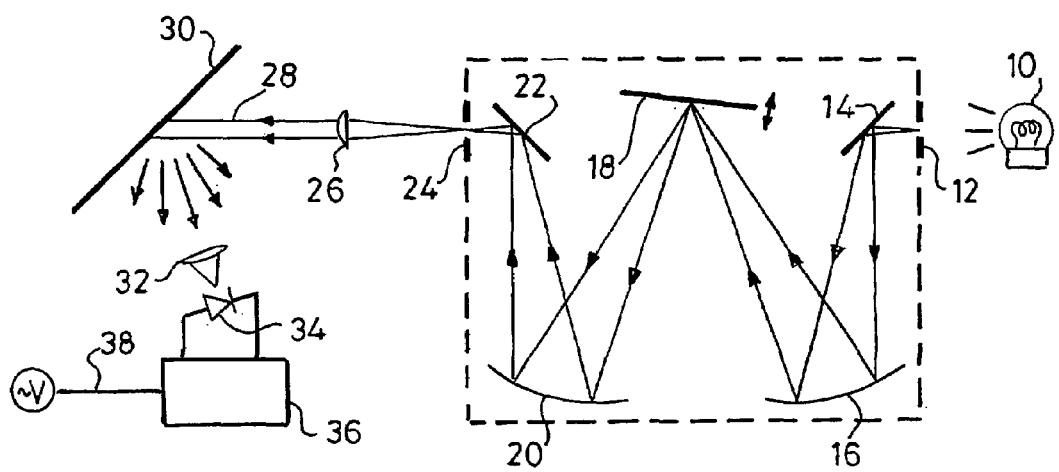
*Fig. 1*
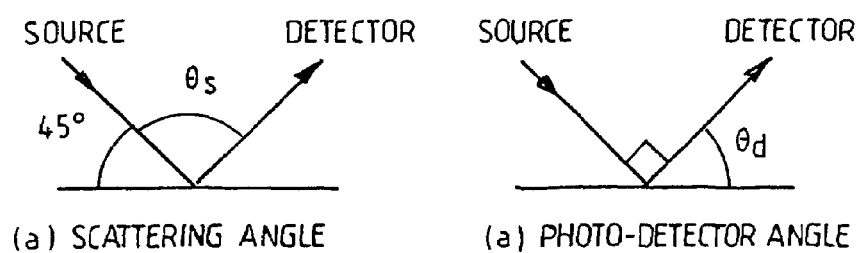
*Fig. 2*  *Fig. 3*

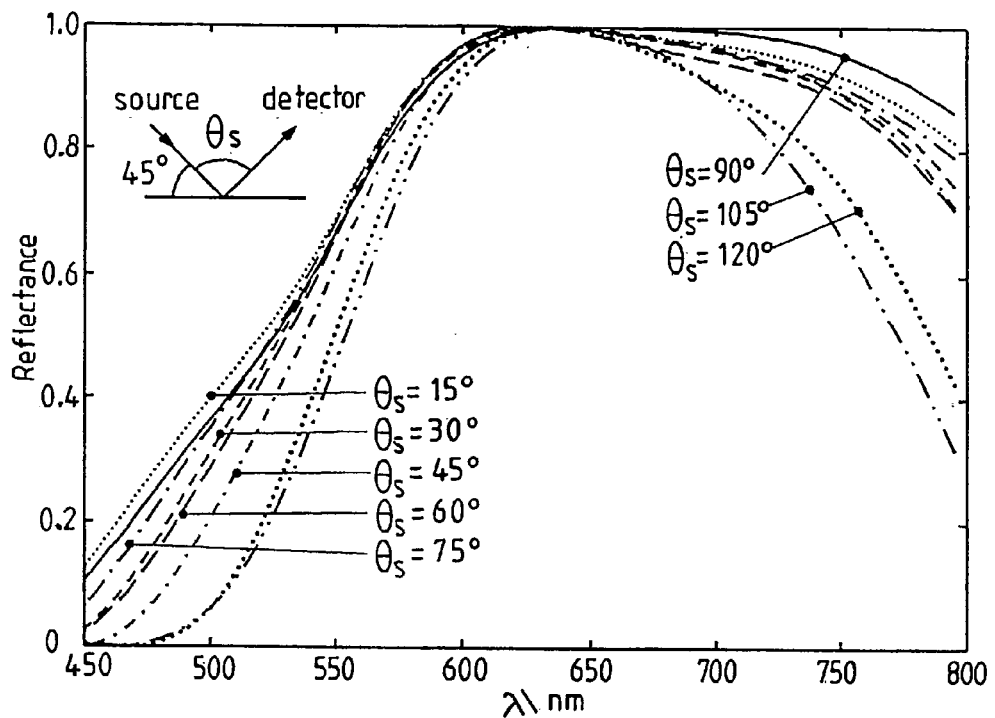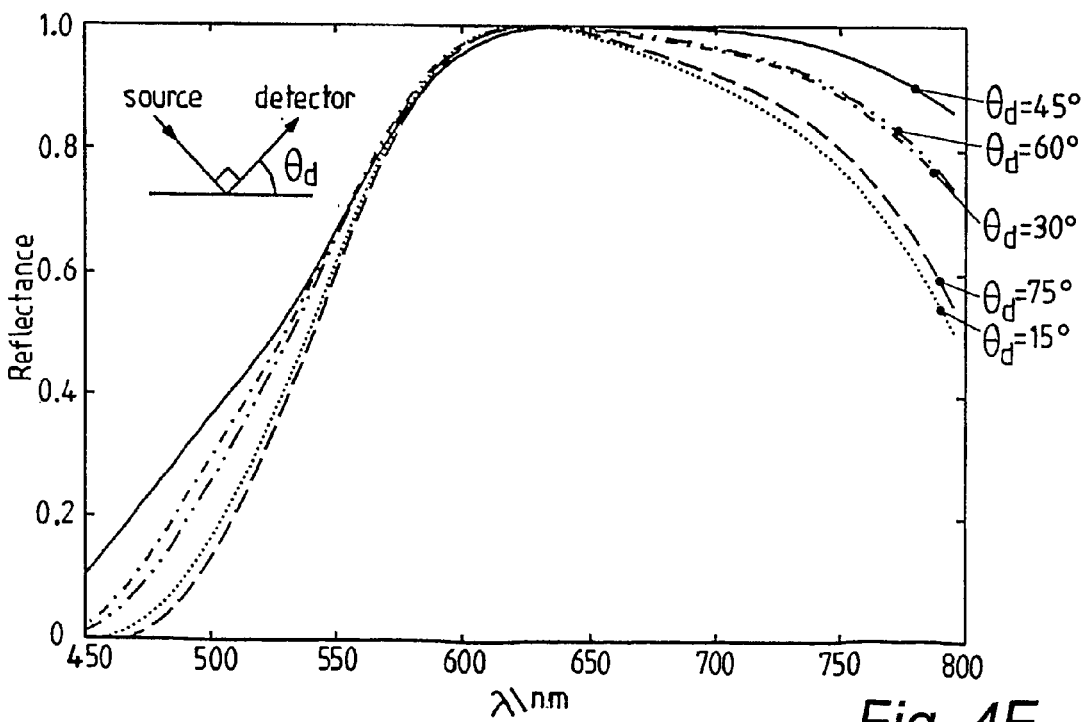
Fig. 4E

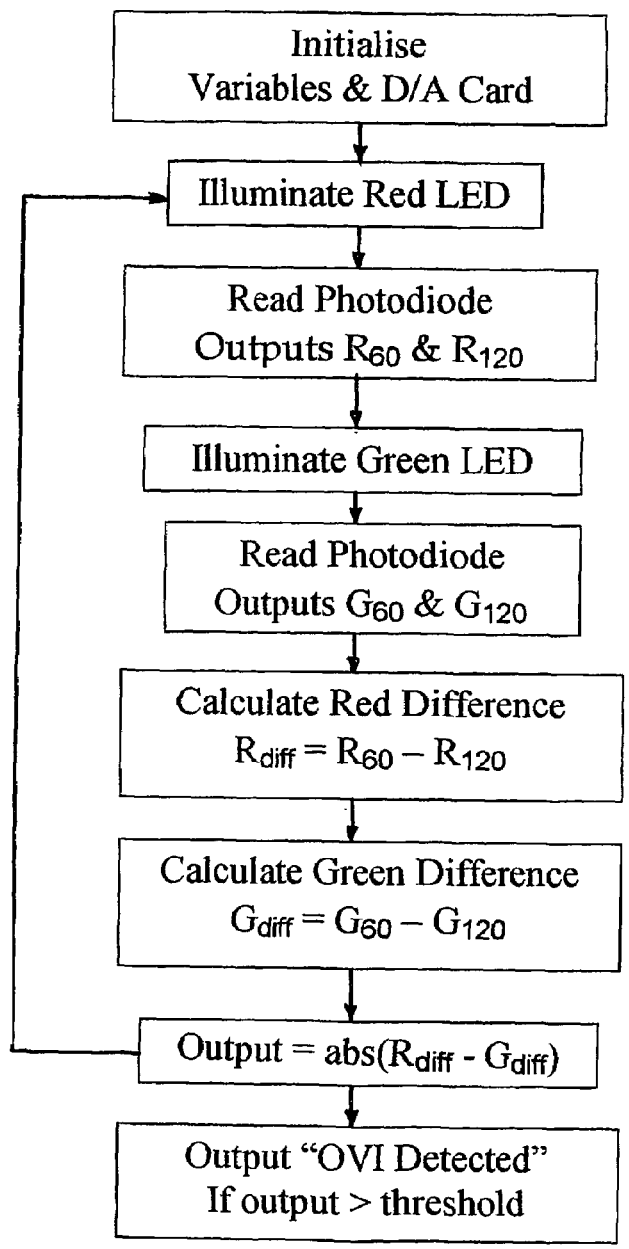
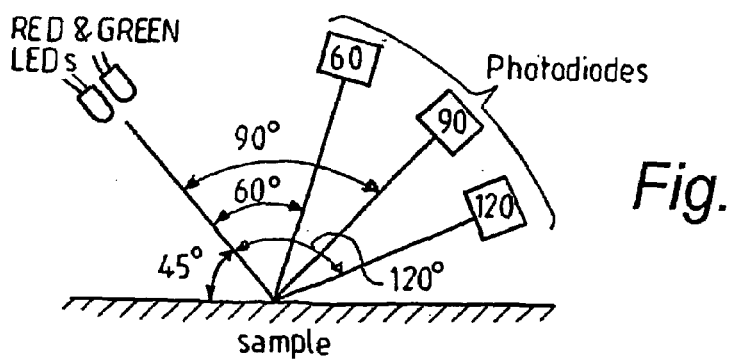
Fig. 12

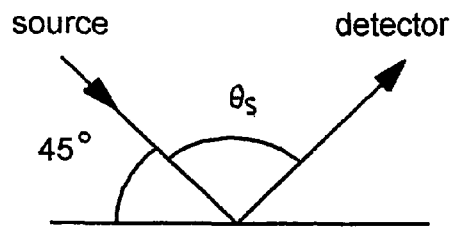
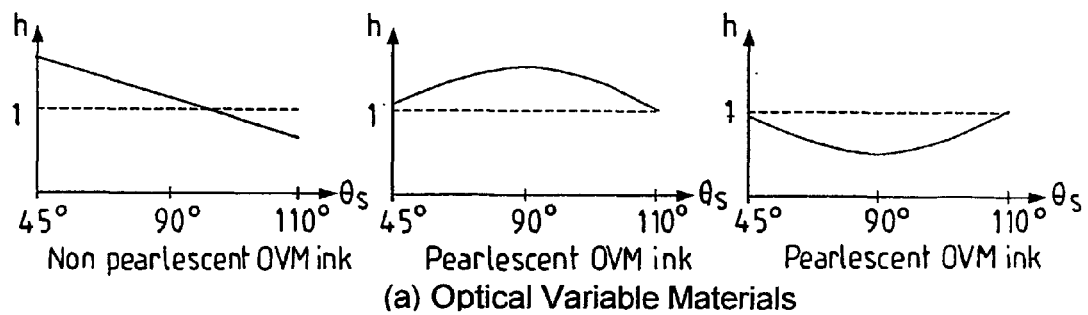
(a) Optical Variable Materials
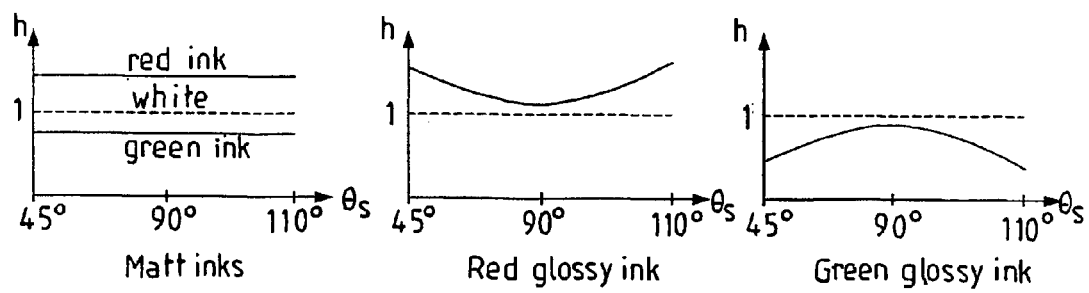
(b) Other Ink Types
Fig. 20

DETECTION OF PRINTING AND COATING MEDIA

FIELD OF THE INVENTION

This invention concerns methods and apparatus for detecting the presence in or on a surface, particularly for identifying the presence of different printing or coating media and particularly detecting and identifying optically variable materials in or on printed or coated surfaces. The invention is especially concerned with the detection of optically variable materials on security documents such as, but not limited to banknotes, passports, driving licences, identity cards, bank and credit cards, security passes, and the like. Typically materials are inks, dyes and varnishes.

BACKGROUND OF THE INVENTION

In the security document printing industry, it is commonplace to provide areas on a document with specific optical characteristics which can be identified by illumination in a predetermined way at a particular wavelength and/or polarisation. Examples include the use of holograms and gratings incorporated onto such documents. It has been proposed to incorporate in or on such a document one or more regions of an Optically Variable Material, henceforth referred to as OVM.

An optically variable material (OVM) can comprise any material which changes colour depending on the angle at which a surface containing the material is viewed, and includes pearlescent materials, iridescent materials, liquid crystalline materials and OV inks such as sold under the trade name OVI by Sicpa SA of Lausanne, Switzerland.

It is a property of an OVM that a region printed or coated using such a material will appear differently coloured depending on the viewing angle and the angle of illumination. In one example if a flat printed surface containing one particular OVM is illuminated by white light at an angle of 45° to the normal, the OVM appears purple to the human eye when back scattered light is viewed, orange when direct (specular) reflection is viewed, and green if viewed along the surface of the paper, that is at a glancing angle.

OVM inks generally fall into two categories, non-pearlescent and pearlescent. The optical characteristics of such inks are different and both again differ from the optical characteristics of a non-OVM (metallic) ink.

It is an object of the present invention to provide a method and apparatus for detecting the presence of an OVM in or on a surface, typically the surface of a security document.

It is another object of the present invention to provide a method and apparatus for detecting, and identifying the type of, OVM in or on a surface, typically the surface of a security document.

It is another object of the present invention to provide a method and apparatus for illuminating, and responding to reflected light from, a surface, and which is adapted to generate a signal indicative of material present in or on the illuminated surface.

SUMMARY OF THE INVENTION

According to a first aspect of the present invention a method of detecting the presence of a non-pearlescent OVM in or on a surface, comprises the steps of illuminating the surface at a first angle to the surface and detecting and determining the frequency spectrum of scattered light in two different directions from the surface, one direction subtending an angle to the surface which is substantially different from the said first angle and is substantially parallel to the plane of the surface, and the other direction subtending an angle to the surface which is substantially closer to the said first angle than the said one direction.

In a preferred method the angle of the one direction to the surface (the second angle) is in the range 1° to 15° and the angle made by the other direction to the surface (the third angle) is within 10° of the said first angle.

In a particularly preferred method the said second angle is 10° and the said third angle equals the said first angle.

According to a second aspect of the present invention a method of detecting the presence of a pearlescent OVM in or on a surface comprises the steps of illuminating the surface at a first angle and firstly detecting and determining the frequency spectrum of substantially direct specular reflection from the surface, and secondly detecting and determining the frequency spectrum of scattered light leaving the surface at an angle which is different from that at which direct specular reflection occurs.

In one method incorporating this second aspect of the invention the second detection is of forwardly scattered light.

Typically the forwardly scattered light is detected at an angle to the said surface which is in the range 1° to 15°, preferably 10°.

In another method incorporating this second aspect of the invention the second detection is of back scattered light.

Typically the back scattered light is detected at an angle within 10° of the direction in which illuminating light is projected towards the surface, and preferably is detected at substantially the same angle as that which the illuminating light makes to the said surface.

In methods incorporating either the first or second aspect of the invention the two detections may be performed in succession one after the other or simultaneously.

Where the detections are performed in succession a single detector may be employed, which is moved between the two positions to allow light which is being reflected from or scattered by the surface in the different directions of interest to be intercepted.

Alternatively where a plurality of detectors is provided each fixed in position to intercept reflected or scattered light as appropriate, the detectors may be separately interrogated either one after the other, to provide a succession of intensity values or simultaneously to provide a corresponding plurality of intensity values.

The spectral determination of the light incident on the or each detector may be performed by the detector if a suitable photo-sensitive element or a combination of one or more filters and at least one photo-detector is employed for the or each detector which will supply different signals or different values of a parameter of a signal, depending on the wavelength of light incident thereon.

The illuminating light may be white light or more preferably the light is made up of two or more distinct monochromatic components having different (known) wavelengths.

According to a third aspect of the present invention a method of determining if a surface contains a specific OVM comprises the steps of illuminating the surface using light containing two substantially monochromatic components of wavelength $\lambda_1$ and $\lambda_2$, detecting the intensity of scattered light from the surface at the two scattering angles $\varnothing_1$ and $\varnothing_2$ selected according to the OVM of interest, computing the magnitude of the difference between the intensity values for $\lambda_1$ light at $\varnothing_1$ and $\varnothing_2$, less the difference between the intensity values for $\lambda_2$ light at $\emptyset_1$ and $\emptyset_2$, and generating an output signal indicating the presence or absence of the specific OVM depending on the computed difference magnitude relative to a predetermined value.

Typically the computed difference value magnitude is compared with the predetermined value to generate a first output signal value indicating the presence of the specific OVM, if the computed magnitude is at least as great as the predetermined value, or a second output signal value indicating that the specific OVM has not been detected, if the computed magnitude is less than the predetermined value.

In a method incorporating the said third aspect of the invention, the surface may be illuminated by the two monochromatic components simultaneously, or preferably separately first with monochromatic light of one wavelength $\lambda_1$ and then with monochromatic light of the second wavelength $\lambda_2$.

Detection may be performed by a single detector which is moved between two positions so as to receive light reflected/scattered from the surface first at one and then the other of the two angles $\emptyset_1$ and $\emptyset_2$, or more preferably by means of two detectors which are positioned so as to receive light from the surface along the directions dictated by $\emptyset_1$ and $\emptyset_2$.

Where one detector is employed the values of signals from it at the two different positions may need to be modified to take account of any inherent differences in intensity of the originating illuminations incident on the surface due for example to different intensity levels and/or any misalignment of the sources of the $\lambda_1$ and $\lambda_2$ light.

Where two detectors are employed the values of the signals from one or both detectors may also need to be modified to take account of any inherent differences in the responses of the two detectors to light of given intensity incident thereon, and any misalignment of the detectors.

A method incorporating the said third aspect of the invention therefore preferably includes a calibration procedure in which the light is projected towards and the reflected/scattered light is received from, a non OVM containing matt white surface.

According to a fourth aspect of the invention, in a method incorporating the said third aspect of the invention the absolute value of the computed difference value may be compared with a range of possible values, the different values in the range corresponding to differing concentrations of the specific OVM in or on the surface under test.

Preferably the light projected onto the surface is collimated.

Where two detectors are employed as is preferred, the signals from each detector may be gated or addressed in synchronism with the changing wavelength of the illuminating light, so that during each gating or addressing period the wavelength of the incident light is known and there is no light of the other wavelength present to confuse matters.

The values of $\lambda_1$ and $\lambda_2$ and $\emptyset_1$ and $\emptyset_2$ are selected by reference to information obtained by interrogating light reflected/scattered by a surface containing the OVM of interest at different angles to the surface, as described herein. By recording the results of such tests at the different angles, two wavelengths and two angles which give best reflection/scatter for those wavelengths, can be determined as being unique to surfaces containing that OVM.

Calculation of the difference magnitude in a way which compensates for variations in intensity between one wavelength component and the other, variations due to misalignment, and variations between detector responses, is achieved by calculating the difference magnitude M using equation (1).

$$M=|(K_1R_1-K_2R_2-A^*(K_1G_1-K_2G_2)| \qquad (1)$$

where R and G represent the reflectance signal intensity values outputted by the photo-detectors at the illuminations of $\lambda_1$ and $\lambda_2$ respectively, the subscripts of R and G denoting measurements made by the two detectors at the scattering angles of $\emptyset_1$ and $\emptyset_2$.

Since adjustment of the relative intensities, alignment of the two sources of $\lambda_1$ and $\lambda_2$ illumination, and alignment of the detectors will cause variation in the magnitude of the detector output signals, the calibration constants $K_1$ and $K_2$ are included to allow for misalignment and differences in the photo-detector responses at $\emptyset_1$ and $\emptyset_2$ scattering angles.

The calibration constants $K_1$ and $K_2$ may be set by adjusting the gains of the detector output signal amplification.

The scalar constant A normalises for differences in the detector responses and alignment relative to the $\lambda_1$ and $\lambda_2$ illuminations.

A method of calibrating the detector involves inserting a plain matt white surface in place of the surface to be tested, and adjusting the values of $K_1$ and $K_2$ so that $K_1R_1=K_2R_2=1$. The scalar A is then adjusted to give M=0 with the matt white surface.

The generation of a YES/NO signal is typically achieved by comparing the computed value of M with a predetermined value T, itself derived by computing M from a surface containing a known minimum concentration of the OVM of interest.

Preferably, a plurality of different values of M are computed using a plurality of samples each containing a different (known) concentration of the particular OVM and storing same to form a range of values of T for comparison with computed values of M from surfaces having an unknown concentration of the OVM thereon.

Substitution of the white surface with a sample having a printed or coated surface allows the sample surface to be checked for the presence of the particular OVM. If the OVM is present, the magnitude of M will equal or exceed the predetermined threshold value T, and if not, the magnitude of M will be less than the threshold.

Since the magnitude of M will vary with quantity of OVM present (i.e. concentration for a given constant area), the range of possible values for M, for a given range of samples each containing the same OVM, can be thought of as comprising a "grey scale" output representative of the quantity of OVM ink present, and to this end a look up memory may be provided for each OVM containing different values of T for differing concentrations of that OVM.

The invention also lies in apparatus adapted to perform any of the methods so far described herein as incorporating or comprising the invention or an aspect of the invention.

According to the invention there is provided apparatus by which an output signal is generated indicative of the presence of a specific OVM in or on a surface under test comprising:

1. A light source which produces and projects along a projection axis monochromatic light at each of two wavelengths $\lambda_1$ and $\lambda_2$ selected according to the specific OVM of interest;
2. Means for locating the surface under test to receive the light with the projection axis at a specific angle to the surface;

3. Two photodetectors, the first of which is located to receive light reflected at a first scattering angle $\varnothing_1$, and the second of which is located so as to receive light reflected at a second scattering angle $\varnothing_2$, from the surface, each photodetector producing an analogue signal indicative of the intensity of light incident thereon;
4. Means for adjusting the intensities of the $\lambda_1$ and $\lambda_2$ illuminations;
5. Means for amplifying the signals from the photodetectors;
6. Means for computing the value of the magnitude of the difference between the amplified intensity values for $\lambda_1$ light reflected/scattered from the surface at $\varnothing_1$ and $\varnothing_2$ less the difference between the amplified intensity values for $\lambda_2$ light reflected/scattered from the surface at $\varnothing_1$ and $\varnothing_2$;
7. Means for generating an output signal dependent on the magnitude of the computed difference value to indicate the presence of the material on the surface.

A YES/NO output signal may be obtained by comparing the output signal with a reference.

Preferably the illumination intensities and the gains of the amplifying means are adjusted to calibrate the apparatus, during a calibration step;

It is preferable for the light source to comprise a pair of LED's, one which emits near monochromatic light at or near $\lambda_1$ and the other at or near $\lambda_2$, and the light from the two LED's is projected along a common axis.

Preferably the angle of incidence of the light upon the surface should be at or close to 45 degrees.

Preferably projected light is collimated.

Preferably the photo-detector means comprises a pair of photo-diodes.

It is preferable for each photo-detector to be associated with a lens for focusing light onto the diode, and that this lens should have an aperture optimised to limit the angular range of scattered light incident on the detector, but allowing appropriate and practicable levels of light through.

It is preferable for the apparatus to include a pulsed power supply for the two LED's such that the two LED's are operated alternately. The repetition rate of the two LED's may be in the range 1 KHz up to 1 MHz or higher, limited only by the time response of the photo-detectors.

The apparatus may be electronically hard wired or may supply signals to, and be controlled by, a computer with a suitable interface and data acquisition card. In the case of a general purpose computer, the chosen method is performed by suitably programming the computer to make measurements on and/or compute differences and/or ratios between, the output signal values to produce a classifying signal for a surface under test.

Typically the interface or the apparatus includes analogue signal amplifying means and an analogue to digital converter for supplying digital signals to the data acquisition card.

Although the method and apparatus so far described enables the presence or absence of specific OVM to be distinguished, according to illumination wavelengths and scattering angles used, and for OVM to be distinguished from certain other OVM and non-OVM, and can produce a "grey-scale" output representative of the amount or quality of an OVM present on a surface, the invention also provides an alternative method and apparatus to distinguish between pearlescent OVM, non-pearlescent OVM, and non-OVM in or on a surface.

According therefore to a fifth aspect of the invention, there is provided a method of determining if a surface contains a specific material comprising the steps of:

(1) detecting the intensity of the light reflected or scattered by the surface at a third angle $\varnothing_3$, such that $\varnothing_1$ corresponds to back scattered light, $\varnothing_2$ corresponds to a near specular reflection, and $\varnothing_3$ corresponds to light leaving the surface at a glancing scattering angle, (2) generating three output signals by computing hue ratios $h_{\varnothing 1}$, $h_{\varnothing 2}$ and $h_{\varnothing 3}$, using the pairs of intensity values from each of the three detectors for the two monochromatic $\lambda_1$ and $\lambda_2$ components of illumination, and (3) comparing the computed hue ratios with a predetermined group of three stored values, obtained by experiment, to generate a final output signal whose value depends on the comparison.

Preferably the intensity values from the detectors are adjusted to compensate for background light by measuring and storing the detector output signal value when a surface is present but no $\lambda_1$ or $\lambda_2$ illumination is incident thereon.

In the fifth aspect of the invention the angles are preferably selected as being $\varnothing_1=45°$, $\varnothing_2=90°$ and $\varnothing_3=110°$.

It has been found that by carefully selecting not only the values for $\varnothing_1$, $\varnothing_2$ and $\varnothing_3$, but also carefully selecting the values of $\lambda_1$ and $\lambda_2$, it is possible to employ the method to indicate not only if a particular OVM is present, but in the case of surface coatings and inks, to indicate whether the coating or ink is a pearlescent OVM, a non-pearlescent OVM, or a non-OVM substance, and in the case of the latter to distinguish between matt and glossy coatings.

Preferred values for $\lambda_1$ and $\lambda_2$ which enable such identification to occur are:

$$\lambda_1=654 \text{ nm and } \lambda_2=574 \text{ nm}.$$

Groups of values for the three hue ratios can be obtained by performing the method according to the fifth aspect of the invention and noting and storing in groups of three, the three hue ratio values for surfaces containing different (known) coatings or inks in a look-up memory, each group of three values having stored therewith or linked thereto data indicating the material producing those three values. This look-up memory can then be employed to identify an unknown material in or on a surface subsequently subjected to the method.

The invention can be employed to distinguish between and thereby identify matt inks, glossy inks, OVM inks, and pearlescent OVM inks and according to the invention a method of determining the material present in or on a surface for which three hue ratios $h_{\varnothing 1}$, $h_{\varnothing 2}$ and $h_{\varnothing 3}$ are determined according to the fifth aspect of the invention as between a matt ink, a glossy ink, an OVM ink, and a pearlescent OVM ink by checking the hue ratios using the following criteria:

(i) if $h_{\varnothing 1}$, $h_{\varnothing 2}$ and $h_{\varnothing 3}$ are substantially constant with scattering angle (and have a value which is not tending to unity) this indicates a matt ink, (ii) if $h_{\varnothing 2}$ tends to unity and $h_{\varnothing 1}$ and $h_{\varnothing 3}$ are significantly different from unity, this indicates a glossy ink, (iii) if $h_{\varnothing 1}$, $h_{\varnothing 2}$ and $h_{\varnothing 3}$ decrease with increasing scattering angle, and the decreases tend to be substantial, this indicates an OVM ink, (iv) if specular reflection produces a more saturated colour resulting in the $h_{\phi 2}$ ratio diverging from unity, this indicates a pearlescent OVM ink.

Preferably the angle of incidence of the illuminating light on the surface is at or near 45°.

Preferably the angles of detection are selected as: $\emptyset_1=45°$, $\emptyset_2=90°$ and $\emptyset_3=110°$ Preferably also the illuminating light is collimated.

The invention also lies in apparatus adapted to perform the modified method provided by the fifth aspect of the invention, comprising:

(1) a light source which produces and projects along a projection axis monochromatic light at each of two wavelengths $\lambda_1$ and $\lambda_2$, (2) platform means for locating a surface under test to receive the light with the projection axis at a specific angle to the platform, (3) three photo-detectors located relative to the platform so as to separately receive reflected/scattered light from a surface thereon at three different angles $\emptyset_1$, $\emptyset_2$, and $\emptyset_3$, where $\emptyset_1$ corresponds to back scattered light, $\emptyset_2$ to near specular reflection and $\emptyset_3$ to light leaving the surface at a shallow angle (a glancing scattering angle), (4) means for adjusting the intensities of the $\lambda_1$ and $\lambda_2$ components of illumination, (5) means for amplifying the signals from the photo-detectors, (6) means for computing the ratio of the response of each photo-detector to the two different wavelengths in the reflected/scattered light incident thereon after taking background light into account, (7) comparator means for comparing the three ratio values so obtained with at least one set of three stored values, and generating an output signal dependent on the comparison.

The comparator means may generate either a YES/NO signal in response to the comparison depending on whether or not the three computed values are similar to the three stored values, or an identification signal indicating which of a plurality of groups of stored values (each comprising a group of three such values) the three computed values most closely correspond.

Preferably the photo-detector output signals are adjusted for background illumination before the hue ratios are computed. Background intensity level is obtained by noting each photo-detector output signal value with the surface in place but when no $\lambda_1$ or $\lambda_2$ illumination is present. This value may be deducted from subsequent output signals from that photo-detector obtained when the surface is illuminated by $\lambda_1$ and $\lambda_2$ illumination.

The apparatus may be electronically hard wired or may supply signals to, and be controlled by, a computer with a suitable interface and data acquisition card. In the case of a general purpose computer, the chosen method is performed by suitably programming the computer to make measurements on and/or compute differences and/or ratios between, the output signal values to produce a classifying signal for a surface under test.

Typically the interface or the apparatus includes analogue signal amplifying means and an analogue to digital converter for supplying digital signals to the data acquisition card.

According to a sixth aspect of the invention a further method of identifying the presence of a particular type of material on a printed or coated surface, comprises the steps of:

1. Illuminating the surface at a pre-set angle to the surface with substantially monochromatic light at three wavelengths $\lambda_1$, $\lambda_2$ and $\lambda_3$ selected in accordance with the particular type of material, 2. Detecting light reflected from the surface at three different angles $\emptyset_1$, $\emptyset_2$ and $\emptyset_3$, one of which $\emptyset_2$ corresponds to a near specular reflection and the other two of which are selected in accordance with the particular type of material and are at or near to those at which the illumination wavelengths give good reflectance changes for the particular type of material.

3. Computing 3 hue values from the intensity values determined by each detector for each of the three monochromatic illumination components $\lambda_1$, $\lambda_2$ and $\lambda_3$, thereby to produce 9 hue values relating to the surface, 4. Comparing the 9 values so obtained with 9 stored hue values, obtained by performing the method on a surface containing some of the particular type of material, 5. Generating a final output signal whose value depends on the comparison.

The final output signal may be in binary format and posses one value only if identity or near identity is obtained by the comparison, thereby indicating that the particular type of material is present.

Preferably the hue values are computed after taking into account and adjusting the photo-detector output signals for any background illumination. This may be achieved by noting the photo-detector output signals with the surface present but in the absence of any $\lambda_1$, $\lambda_2$ or $\lambda_3$ illumination.

Preferably the comparison is performed by calculating the nearest neighbour classifier using the 9 stored hue values for the particular material.

The nearest neighbour classifier may be computed by summing the squares of the differences between the computed hue values and stored hue values and comparing the sum with a threshold. In the case of identity the value of the sum is zero and near identity situations can be identified if the sum value is less than a small numerical value selected for the threshold.

Computation of the nine hue values $r_{\phi 1}$ $g_{\phi 1}$ etc., for the three detectors receiving reflected/scattered light at the angles $\emptyset_1$, $\emptyset_2$ and $\emptyset_3$ at the wavelengths $\lambda_1$, $\lambda_2$ and $\lambda_3$, each of which produces an intensity value in the detector output of $R_\phi$, $G_\phi$, or $B_\phi$ respectively, and where the background illumination produces an intensity value $D_{\phi 1}$, $D_{\phi 2}$ etc., in the detector output, is achieved by using the equations:

$$r_{\phi 1}=(R_{\phi 1}-D_{\phi 1})/(R_{\phi 1}+G_{\phi 1}+B_{\phi 1}-3D_{\phi 1})$$

$$g_{\phi 1}=(G_{\phi 1}-D_{\phi 1})/(R_{\phi 1}+G_{\phi 1}+B_{\phi 1}-3D_{\phi 1})$$

$$b_{\phi 1}=(B_{\phi 1}-D_{\phi 1})/(R_{\phi 1}+G_{\phi 1}+B_{\phi 1}-3D_{\phi 1})$$

$$r_{\phi 2}=(R_{\phi 2}-D_{\phi 2})/(R_{\phi 2}+G_{\phi 2}+B_{\phi 2}-3D_{\phi 2})$$

$$g_{\phi 2}=(G_{\phi 2}-D_{\phi 2})/(R_{\phi 2}+G_{\phi 2}+B_{\phi 2}-3D_{\phi 2})$$

$$b_{\phi 2}=(B_{\phi 2}-D_{\phi 2})/(R_{\phi 2}+G_{\phi 2}+B_{\phi 2}-3D_{\phi 2})$$

$$r_{\phi 3}=(R_{\phi 3}-D_{\phi 3})/(R_{\phi 3}+G_{\phi 3}+B_{\phi 3}-3D_{\phi 3})$$

$$g_{\phi 3}=(G_{\phi 3}-D_{\phi 3})/(R_{\phi 3}+G_{\phi 3}+B_{\phi 3}-3D_{\phi 3})$$

$$b_{\phi 3}=(B_{\phi 3}-D_{\phi 3})/(R_{\phi 3}+G_{\phi 3}+B_{\phi 3}-3D_{\phi 3})$$

where $R_{\phi 1,2,3}$ are $\lambda_1$ illuminated signal from detectors at scattering angles of $\emptyset_1$, $\emptyset_2$, and $\emptyset_3$ respectively; $G_{\phi 1,2,3}$ and $B_{\phi 1,2,3}$ are the same but for $\lambda_2$ and $\lambda_3$ illumination respectively.

Calibration may be achieved by performing the method using a surface containing the particular material of interest and computing the 9 values $r_{\phi 1}$, $g_{\phi 1}$ etc., and storing the computed values as $\alpha_1$, $\alpha_2$, $\alpha_3$, $\beta_1$, $\beta_2$, $\beta_3$, $\gamma_1$, $\gamma_2$, $\gamma_3$.

Nearest neighbour computation may be performed using the following formula:

$$D = (r_{\phi 1} - \alpha_1)^2 + (g_{\phi 1} - \beta_1)^2 + (b_{\phi 1} - \gamma_1)^2 +$$
$$(r_{\phi 2} - \alpha_2)^2 + (g_{\phi 2} - \beta_2)^2 + (b_{\phi 2} - \gamma_2)^2 +$$
$$(r_{\phi 3} - \alpha_3)^2 + (g_{\phi 3} - \beta_3)^2 + (b_{\phi 3} - \gamma_3)^2$$

The method just described may be used to distinguish between OVM's, non-OVM's and matt and glossy inks, and also enables small variations in OVM quality or quantity to be detected. Tolerance to such variations can be increased by altering the value of the threshold, albeit at the expense of the likelihood of miss-classification.

Multiple material type classifications can be performed by pre-storing different $\alpha$, $\beta$, $\gamma$ values for different pre-measured samples and performing nearest neighbour threshold classification using each of the stored $\alpha$, $\beta$, $\gamma$ value sets, until the lowest value of the sum is obtained, indicating the best match.

Apparatus adapted to perform the method of the sixth aspect of the invention comprises:

(1) three monochromatic light sources producing light of $\lambda_1$ $\lambda_2$ and $\lambda_3$ wavelengths, the particular wavelengths being selected in relation to the material to be identified, (2) means for projecting the light at a particular angle towards a support means on which a sheet of material the surface of which is to be investigated can be laid, the angle being selected in relation to the materials to be identified, (3) three photo-detectors arranged relative to the support means to receive reflected/scattered light along three different directions therefrom, the directions being selected in relation to the material to be identified;

(4) computing means adapted to receive intensity signals from the three detectors and compute therefrom nine hue values corresponding to ratios of intensity signal values and combinations of such signal values, from each detector;

(5) memory means adapted to store at least one set of nine hue values obtained by using a sheet of material containing at least in or on the surface thereof the material which is to be looked for in other surfaces, (6) comparison means for comparing computed and stored hue values to generate a binary output signal one value of which is generated only if identity or near identity exists between the computed and stored hue values.

Preferably the hue values are computed after taking into account, and adjusting the photo-detector output signals for, any background illumination. This may be achieved by noting the photo-detector output signals with the surface present but in the absence of any $\lambda_1$, $\lambda_2$ and $\lambda_3$ illumination.

The comparison means may comprise a computing means adapted to compute the sum of the squares of the differences between the computed and stored hue values.

Preferably the projection angle is 45°.

Preferably collimating means is provided to collimate the projected light.

Preferably each photo-detector comprises a photo-diode.

Preferably lens means is provided for focusing reflected/scattered light from the surface onto the photo-diode.

Preferably the lens means has an aperture which is selected so as to limit the angular range of scattered light which will reach its associated photo-detector.

Preferably each of the monochromatic light sources is an LED.

It is preferable for the apparatus to include a pulsed power supply for the LED's, such that the three LED's are operated alternately in series, with an off period to allow background light to be measured. The repetition rate of the LED's preferably occurs in the range 1 KHz up to 1 MHz, or beyond and is only limited by the time response of the photo-detectors.

The apparatus may be electronically hard wired or may supply signals to, and be controlled by, a computer with a suitable interface and data acquisition card. In the case of a general purpose computer, the chosen method is performed by suitably programming the computer to make measurements on and/or compute differences and/or ratios between, the output signal values to produce a classifying signal for a surface under test.

The invention also lies in a method of identifying a material in or on a surface comprising performing any two or more of the different methods as aforesaid in parallel, on output signals from photo-detectors in receipt of light from the surface at two or more different angles, and generating a final classification or acceptance signal depending on the results obtained from the two or more identifications, and in apparatus adapted to perform in parallel the two or more methods as aforesaid.

By the expression in parallel is meant simultaneously in time, or one after the other in quick succession with the results of the first method being stored for combining with the results of the second and any other method to produce the final classification or acceptance signal.

Typically the interface or the apparatus includes analogue signal amplifying means and an analogue to digital converter for supplying digital signals to the data acquisition card, or the latter includes an A/D converter.

The invention is of particular use in the field of article authentication, such as checking passports, ID cards, driving licences, bank notes, bonds, share certificates, postage stamps, and other security documents, although it is to be stressed that the invention is not limited to this type of use, and the above are in any case only intended as examples of documents which can be checked.

In so far as inks, dyes and varnishes can be applied to any suitable surface, the invention is not limited to the authentication of documents, but can be used in connection with any article having a suitable surface to which an OVM can be applied.

In general the area of the coated or impregnated surface which is to be illuminated and from which reflected/scattered light is to be detected, needs to be flat. However the area concerned need only be relatively small, but if so the area on which the illuminating light is to fall needs to be restricted so as to correspond to the size of the flat area which can be checked using reflected/scattered light therefrom.

It is worth noting that the time required for a test to be performed can be very short if the light illuminating the surface can be turned on and off very quickly and the detector can respond equally quickly. Therefore provided articles can be presented to and removed from an illuminating and detecting device at high sped, and can be routed differently after presentation, depending on whether the light received by the detector causes an appropriate signal to be generated or not, the speed at which articles can be detected is more likely to be limited by the speed at which they can be moved into and out of the position at which the test can be performed, rather than on the speed at which the test can be performed by the device.

Although the ability to perform a test on a surface very quickly enables the invention to be incorporated into a process requiring a large number of articles to be checked per minute, it is not limited to such applications, and it may be employed in a device to which articles are supplied on an occasional basis, such as an off-line security document verification/authentication device. The result of the test to establish whether the article is genuine or not will be available almost instantaneously, thereby involving little or no delay in the processing of articles which need to be verified/authenticated.

The invention may be employed in the field of quality control for on-line checking that particular inks, dyes or variables have been satisfactorily applied to articles. Thus the invention is of application in the field of on-line checking of OVM coated sheet material before, during or after being printed or coated with other non-OVM material, depending on whether the OVM material is applied to the sheet material before during or after the other non-OVM material is applied thereto.

The invention may thus be employed in the quality control of sheet material which is to be printed to form security documents such as bank notes where OVM is applied to some or all of the surface of the sheet material before it is printed to form the documents.

The invention may also be employed in the quality control of a process of printing sheet material in which OVM is applied to the surface of the sheet material during or after the printing process.

In the field of quality control of coated sheet material linear speeds of the sheet material of the order of 2.4 meters per second are typical.

Bank note sorting as between one denomination and another or separating possible forgeries from genuine notes using currently available identification techniques, is typically performed with linear speeds of the notes through the inspection station of the order of 10 meters per second. However the speed of operation of apparatus operating in accordance with the present invention, to sort notes incorporating OVM on the basis of OVM response criteria, will enable linear speeds of notes through the inspection station to be at least 20 meters per second.

The invention therefore also lies in a method of checking an article containing OVM in at least some of the surface to determine if the correct OVM has been employed, in which a surface of the article is illuminated and light scattered/reflected from the surface is detected and an output signal generated in accordance with any of the previously described methods for detecting or determining an OVM in or on a surface, and in which an appropriate criterion is selected for generating an acceptance signal therefrom.

The invention also lies in a method of checking an article containing a particular OVM to determine if the OVM is present in a particular region of a surface of the article, in which the article is positioned relative to a source of illumination and to detectors for receiving reflected/scattered light therefrom, with only the particular region of the surface being subjected to the illumination, and an output signal is generated in accordance with any of the previously described methods for detecting or determining an OVM in or on a surface, and in which an appropriate criterion is selected for generating a final output signal indicating whether or not the particular OVM is present.

The invention also lies in a method of checking an article containing OVM in at least some of its surface to determine if the latter is present above some minimum concentration measured as quantity of OVM per unit area, in which the article is positioned so that the surface will be illuminated and light reflected/scattered therefrom will be detected and an output signal will be generated in accordance with any of the previously described methods for detecting or determining OVM content of a surface, and in which an appropriate criterion is selected for generating a final signal indicating whether or not a particular concentration of the OVM is present.

The invention also lies in checking apparatus for performing any of the aforesaid methods of checking an article.

In any of the foregoing methods or apparatus the sheet/substrate/article containing the surface of interest may be static or moving during the illumination step, and may be undergoing printing or coating with the OVM and/or other materials, or may have been so printed or coated in a previous process, or may comprise a finished article such as a security document.

Checking apparatus as aforesaid may be fitted to or located downstream from a coating or printing apparatus applying at least OVM to sheet material passing therethrough to thereby enable on-line checking of OVM applied to the sheet material by the coating or printing apparatus, to be monitored.

Checking apparatus as aforesaid may be fitted to a document handling apparatus to enable documents to be sorted according to the OVM found to be present in or on a surface of each document.

Checking apparatus as aforesaid may be incorporated in a cash dispensing machine, a banknote acceptor, or banknote-sorting machine in which the banknotes incorporate OVM in or on their surface.

The invention will now be described by way of example with reference to the accompanying drawings in which:

DESCRIPTION OF DRAWINGS

FIG. 1 illustrates an optical arrangement by which the reflectance of different inked/coated surfaces can be determined in relation to the wavelength of the incident light, for different incidence and observation angles, FIG. 2 is an explanatory diagram indicating scattering angle ($\theta_s$), FIG. 3 is a similar diagram indicating photo-detector angle ($\theta_d$), FIGS. 4A, 4B, 4C, 4D and 4E are graphical illustrations of experimental results obtained for the spectral properties of different sample inks using the system of FIG. 1, FIGS. 12, 13 and 14 are exemplary computer programs for controlling and handling output signals from the detectors of FIGS. 9–11.

FIG. 20 is graphical illustration of hue ratio relationships with scattering angle for different ink types—also used to derive a logic table for use in method II.

DETAILS OF TABLES 1, 2 AND 3 SET OUT AT THE END OF THIS DESCRIPTION

Table 1 is a listing of the different hues observed at different viewing angles, for each of twelve sample inks (numbers 1–12 in the Table).

Table 2 indicates the optimal detector angles using 45° incident light and the optimal detection wavelengths of the twelve sample inks of Table 1, and additionally classifies a sample as OVM, pearlescent OVM or metallic.

Figure 9:
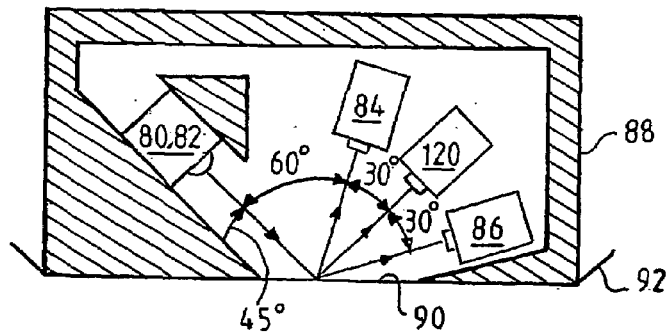
FIG. 9 is a layout diagram of an optical arrangement containing a viewing window, two LED light sources and three detectors, for determining the reflectance characteristics of a printed/coated surface in the viewing window, for use with and A–D converter and digital signal processing computer.
Figure 10:
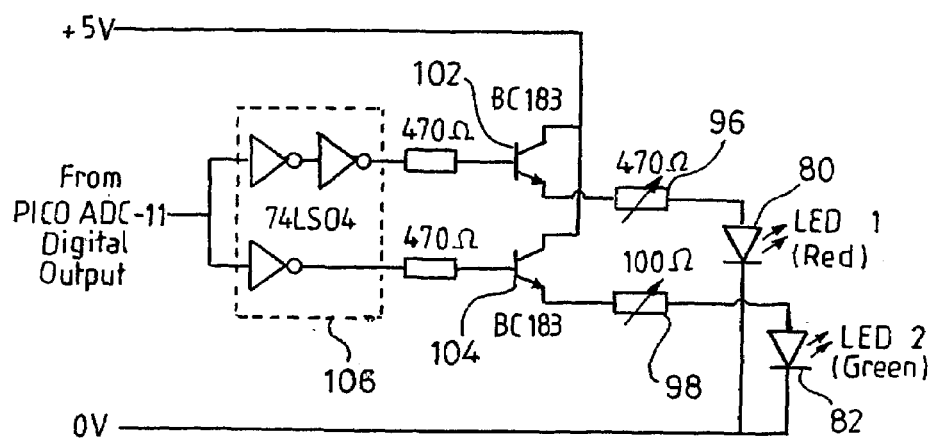
FIG. 10 is a schematic diagram of the control circuit for alternately powering the two LED sources of FIG. 9, using digital signals derived from an A–D converter driven by the computer.

Table 3 lists the hue ratios measured for several sample materials by an arrangement based on FIGS. 9 & 10 using two illumination wavelengths at 654 nm and 574 nm, and three photo detector scattering angles of 45, 90 and 110 degrees.

Table 1 shows details of the visual properties of commercially available OVM inks. These inks generally fall into two categories, non pearlescent and pearlescent. In Table 1 inks 1, 2, 3 and 12 are examples of non-pearlescent OVMs, inks 5 to 11 are pearlescent and ink 4 is a metallic ink which is not an OVM, and is thus viewed as the same colour regardless of viewing angle.

DETAILED DESCRIPTION OF THE DRAWINGS

The optical reflectance characteristics of a surface coated with an ink can be determined as a function of wavelength using a standard commercially available spectrometer set up as shown in FIG. 1.

Thus in FIG. 1 light from a broad band (white light) lamp 10 is projected through a slit 12 onto a plane mirror 14 from where it is reflected onto a first convex mirror 16. Light from 16 is diverted towards a reflection grating 18 after which a similar path via a second convex mirror 20 and plane mirror 22 leads to an exit slit 24 at the focal point of the second convex lens (taking into account the path change introduced by mirror 22).

After passing through the exit slit 24 the now diverging light beam is collimated by a convex lens 26 and a parallel beam of monochromatic light 28 is projected onto the inclined surface of a test sample 30.

Light reflected by the latter is focused by an imaging lens 32 onto a photodiode 24 the output of which is amplified by amplifier 36 to provide an output signal at 38.

By locating the convex mirrors 16 and 20 equidistant from the slits 12 and 24 and the grating 18, respectively, so the mirror 16 forms an image of the slit 12 on the grating, and the mirror 20 forms an image of the slit image reflected by the grating at the slit 24.

Altering the angle of the grating 18 alters the wavelength of the light in the reflected beam travelling towards the prism 20, and items 12 to 24 comprise a known Hilger-Watts monochromator.

Tests on a particular sample 30 involve rotating the grating 18 and observing how the signal at 38 changes. The variation of signal can be plotted relative to wavelength (which is proportional to the tilt angle of 18).

A second test can be performed by selecting particular wavelengths (by appropriate adjustment of the tilt angle of 18) and/or moving the position of the lens and photodiode combination 32, 34 relative to sample 30, so as to view the surface of the sample at different angles, for each wavelength of the illuminating light. In these tests the angle of illumination remains constant.

A third test involves performing Test 2 with the sample 30 set on other angular orientations relative to the axis of the beam 28 and altering the angle of the sample 30 relative to the axis of beam 28 while making adjustments to the position of the lens/diode simultaneously altering the position of the diode combination 32, 24 to maintain a constant included angle between the beam 28 and the optical axis of line 32.

In Test 2 and Test 3 the variation of the signal at 38 can be observed (and plotted if desired) vis a vis the viewing (or observing) angle in Test 2, and illumination/viewing angle variation in Test 3.

A set of curves can be obtained by varying the wavelength of the light impinging on the sample 30 for each of the different angles in each test.

Figure 4A:
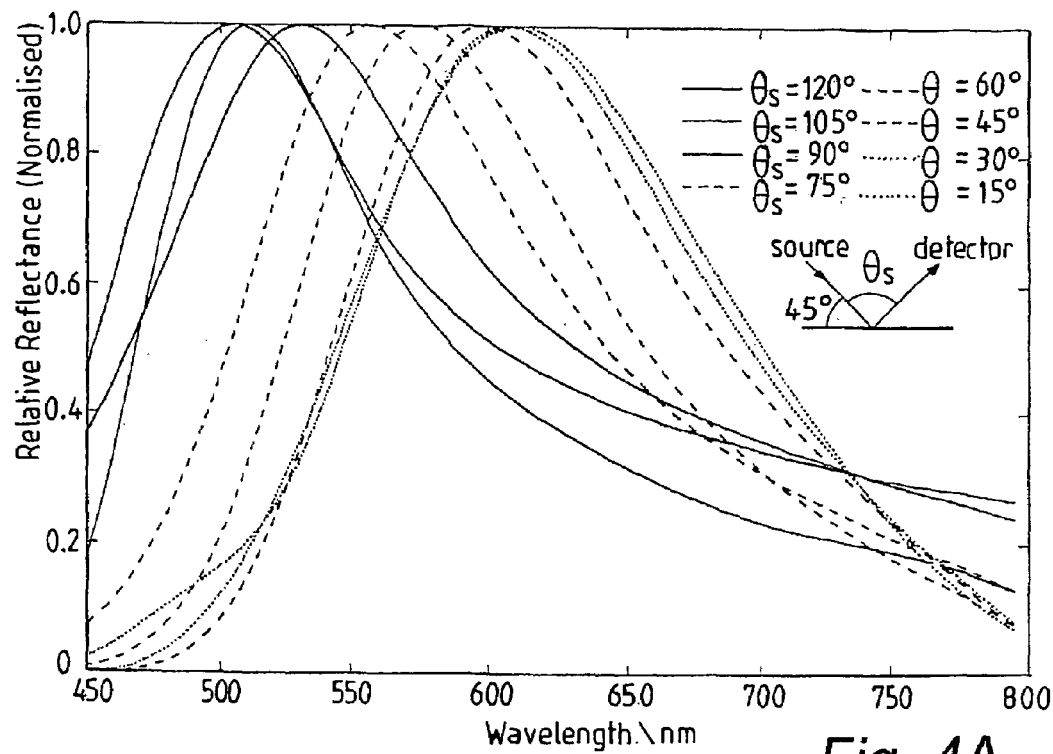
Figure 4B:
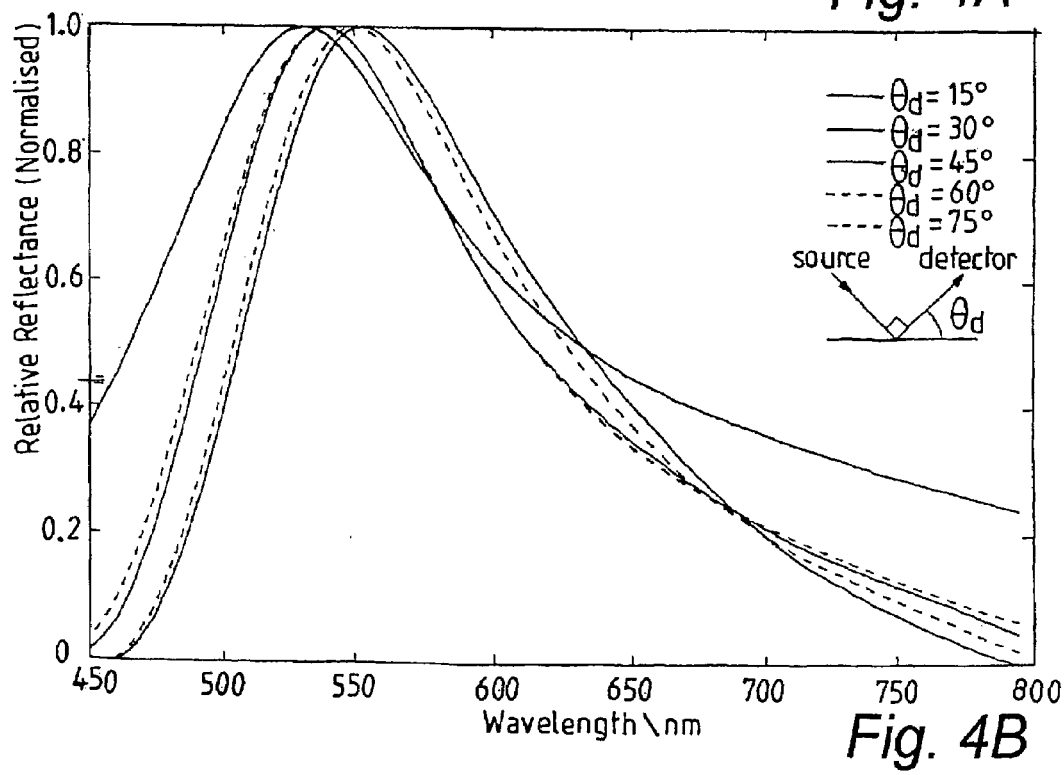

FIGS. 4(a) and 4(b) illustrate a set of curves obtained using a surface coated/printed with ink sample 2 of Table 1. FIG. 4(a) corresponds to Test 2 and FIG. 4(b) corresponds to Test 3 above. In each case the variations of signal at 38 against wavelength is plotted for each of a number of different angles $\theta_s$ (15°–120°) in FIG. 2(a) and $\theta_d$ (15°–70°) in FIG. 2(b).

Again using the system of FIG. 1 optical reflectance characteristics have been determined for all 12 inks of Table 1, for two different viewing and illumination configurations as follows:

(i) Collimated illumination is incident upon the ink at a pre-set angle of 45° to the normal, and the reflectance spectrum is recorded as a function of the scattering angle $\theta_s$—that is the angle between the illumination source and the photo-detector as defined in FIG. 2(*a*).

(ii) Scattering angle is fixed at 90° and the reflectance spectrum is measured by varying just the angle $\theta_d$ of the photo-detector with respect to the paper, as defined in FIG. 2(*b*).

Figure 4C:
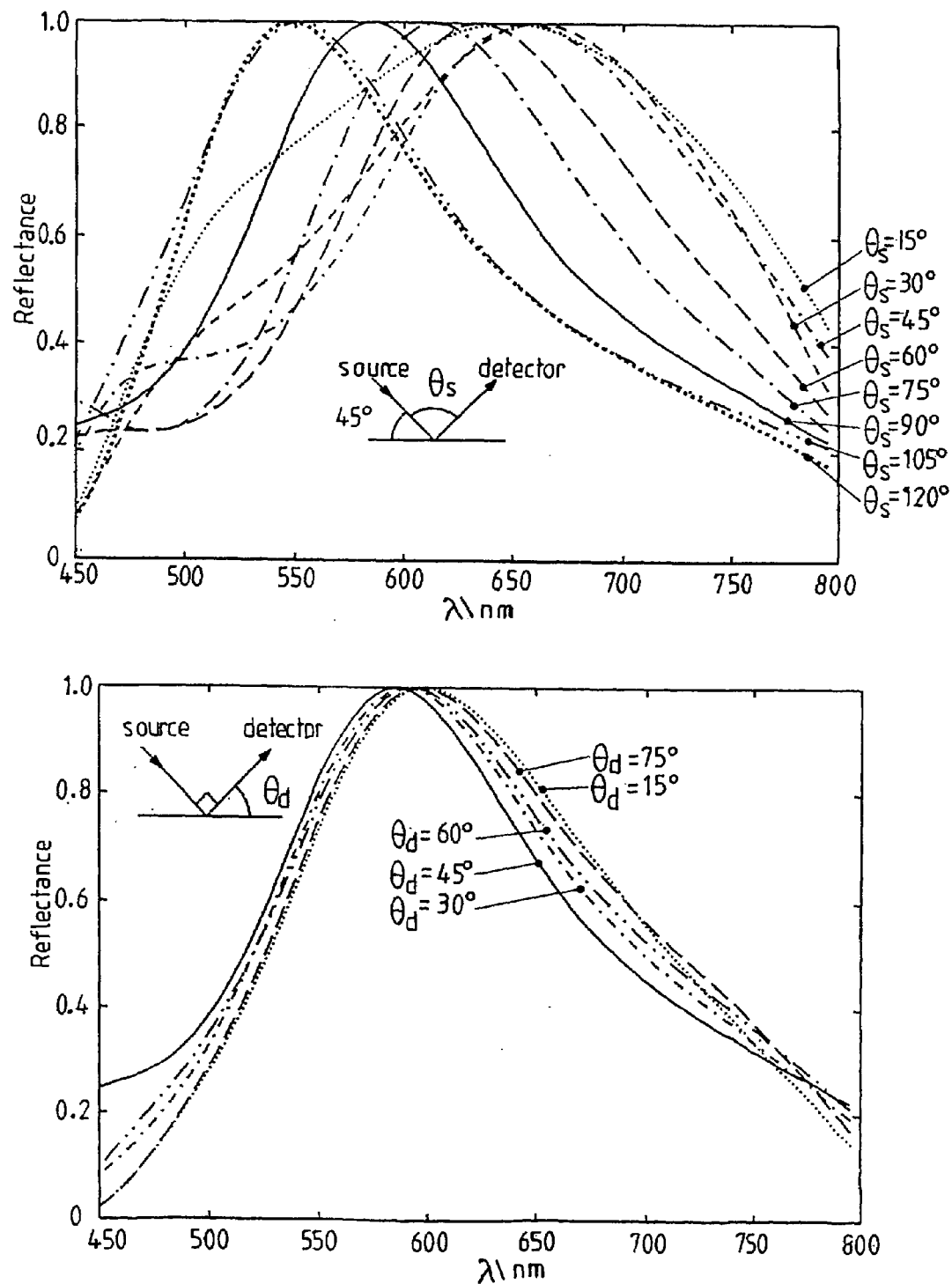
Figure 4D:
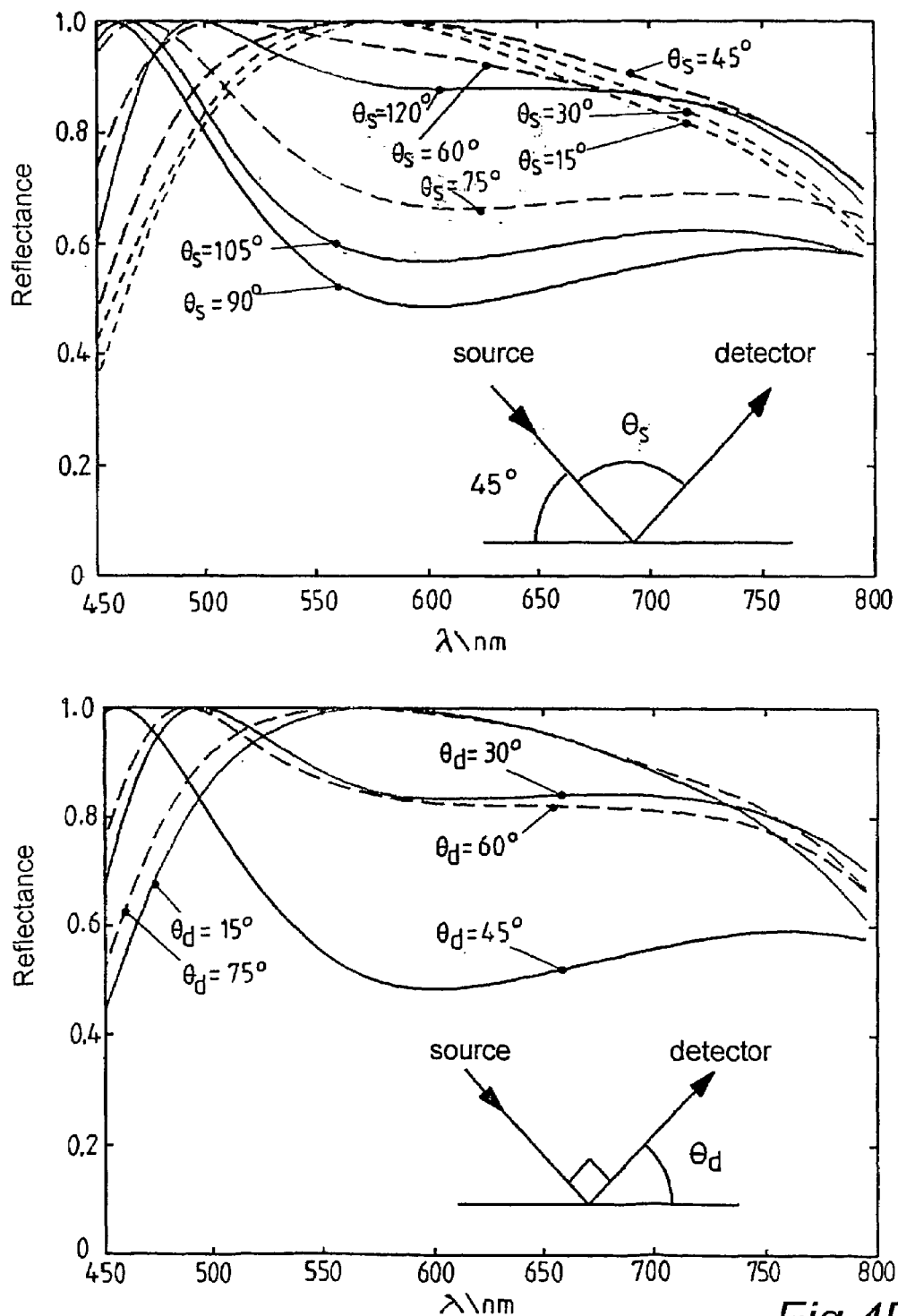

The following properties have been observed for the respective ink types:

1. Non-pearlescent OVM inks (Samples 1, 2, 3 & 12)—these inks exhibit a definite reflectance peak with a half width of about 130 nm, which shifts towards the blue end of the spectrum with increasing scattering angle. This is shown in the upper graph of FIG. 4C for ink Sample 1. When the scattering angle is held constant only slight shifts in the peak are observed with detector angle, as shown in the lower graph of FIG. 4C for ink Sample 1.
2. Pearlescent OVM inks (Samples 5 to 11)—the reflectance spectrum of these inks are relatively flat for almost all illuminating and viewing angles, hence appearing "almost" white. The exception to this is when direct specular reflection is viewed ($\theta_d=\theta_s=90°$) at which a perturbation over a broad wavelength range is observed giving rise to the observed increase in colour. This is shown in FIG. 4D for Sample ink 10.
3. Non OVM metallic ink (Sample 4)—very little change in the spectrum is observed with scattering and detector angles, as shown in FIG. 4E.

From the acquired data, the optimal wavelengths and angles for detection for the twelve sample inks have been determined and are shown in Table 2.

First Detector and OVM Detection Method

Figure 5:
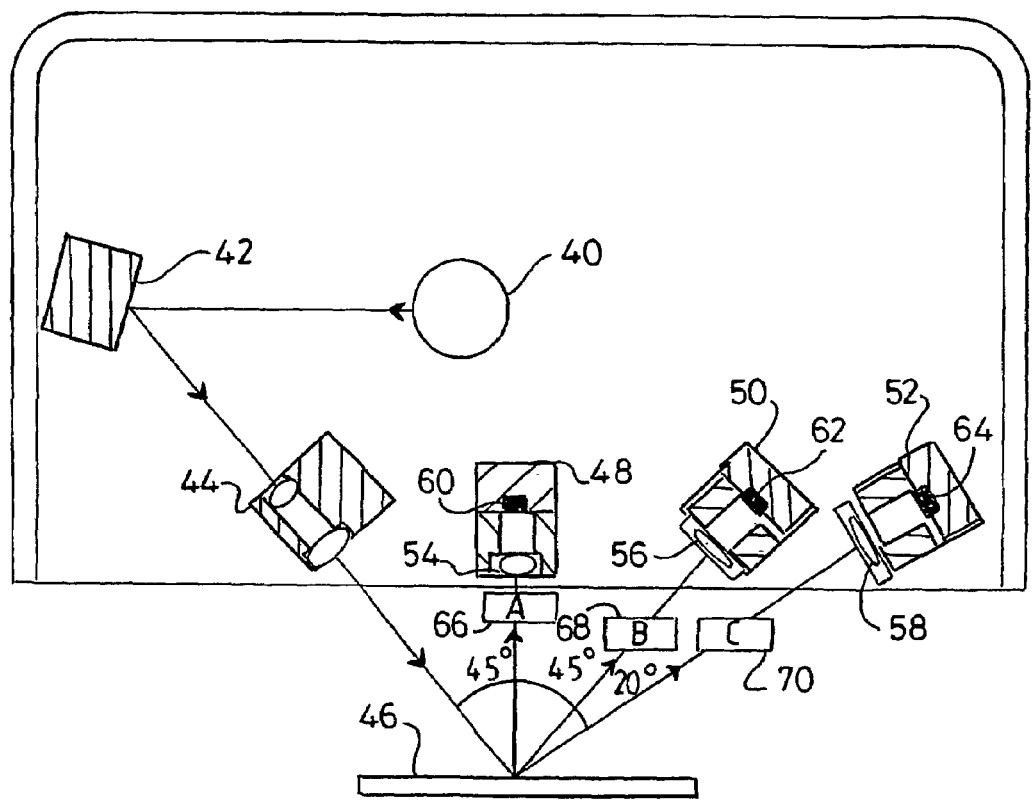
FIG. 5 is a layout diagram of an optical arrangement for determining reflectance characteristics of a surface.

FIG. 5 shows one detector arrangement by which up to three output signals at up to three different detector angles can be obtained using white light to illuminate a sample. As shown a white light source 40 projects light via a mirror 42 and imaging optics (lens assembly) 44 onto a sample surface 46. Reflected/scattered light is viewed at three different angles to the surface by three photodiodes located in housings 48, 50 and 52 each containing an imaging lens 54, 56, 58 and a photodiode 60, 62, 64 respectively.

If the surface 46 is plain white (or a matt ink of uniform colour) the light incident on each of the photodiodes 60, 62 and 64 will be of substantially the same frequency spectrum. However if the surface contains OVM the wavelength of light directed towards 60 may be different from that directed towards 62 and that may be different again from that directed towards 64.

In order to determine if an OVM is present, it is necessary to determine whether the light reflected along the different directions is of a particular wavelength. Depending on the criterion based on Tests 1, 2 or 3 above or the algorithm selected to process the values of output signals from the photo-detectors (see methods I, II and III later) so the outputs from either two or all three of the photo-detectors are required. To cover both possibilities three filters are provided at 66, 68 and 70 each being a band pass filter restricting the unattenuated light to a specific wavelength or narrow band of wavelengths.

Alternatively or additionally similar filters (not shown) may be employed between the source 40 and mirror 42 or between the latter and the lens assembly 44 to restrict the light incident on the surface at any one time, to one of a plurality of different wavelengths.

A plurality of filters may be employed in groups of two or three and different groups selected to produce and/or look for different wavelengths of light both towards the surface and/or along the two or three reflection paths from the surface required for any particular algorithm.

A disadvantage of this arrangement is that much of the light from the source 40 is unavailable for detection by the photodiodes, since broadband white light is employed. However the arrangement does not require monochromatic light sources to be employed.

Alternative OVM Detectors and Methods of Detecting OVM

The following alternative arrangements require monochromatic light sources.

The following alternative detectors have been developed to identify and quantify the presence of an OVM on a surface, and some are adapted to be controlled by and to supply output signals to a commercially available computer fitted with a data acquisition card.

Figure 6:
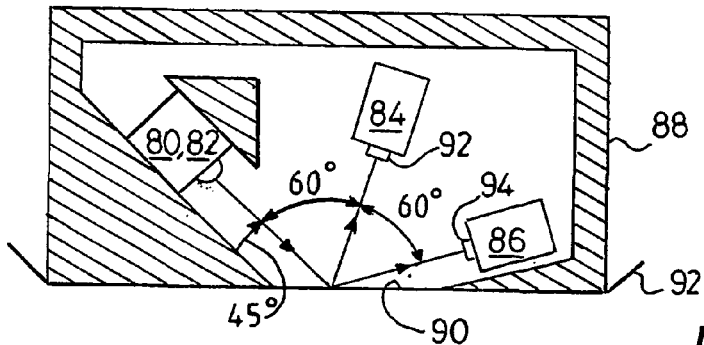
FIG. 6 is a layout diagram of an optical arrangement containing a viewing window, two LED light sources and two detectors for determining the reflectance characteristics of a printed/coated surface in the viewing window.

In FIG. 6, 2 LEDs 80, 82 and two photodiodes 84, 86 are arranged in a light-tight housing 88 relative to a window 90 through which the surface of a sheet of material 92 stretched across or moving below the underside of the housing 88, can be illuminated (by the LEDs) and viewed (by the photodiodes). The light from the LEDs is directed towards the window and each of the diodes 84, 86 includes a lens 92, 94 and receives light reflected from the surface below the window, at 60° and 120° respectively.

Figure 7:
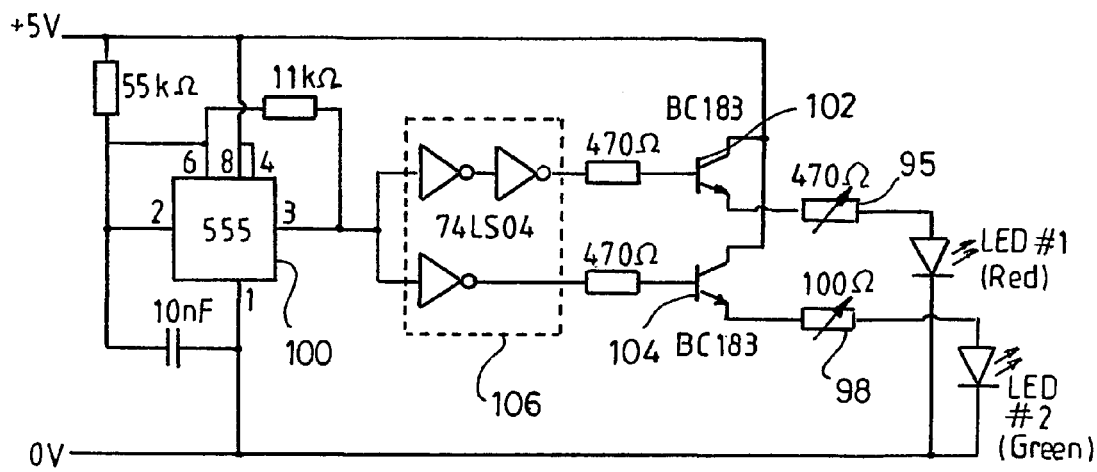
FIG. 7 is a schematic diagram of the control circuit for alternately powering the two LED sources of FIG. 6.

The LEDs are powered alternately from a switched power supply such as shown in FIG. 7. The light output from each LED and the balance between them can be adjusted by altering the value of the variable resistors 96, 98. Timer 100 produces switching pulses at 5 KHz to trigger first one and then the other of two semiconductor devices 102, 104 and the logic device 106 ensures that if 102 is conducting 104 is non-conducting and vice versa.

The switching speed can be set at any frequency governed by the response of the photodiodes 84, 86. Ideally the switching is set to occur at a high frequency such as 1 MHz and the components 84, 86, 100, 104 and 106 would be chosen accordingly.

Figure 8:
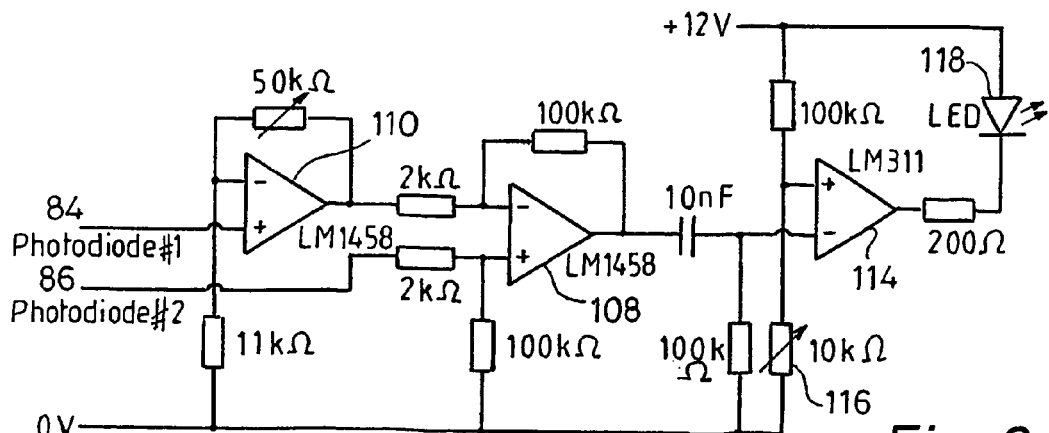
FIG. 8 is a schematic diagram of a classification circuit adapted to receive analogue signals from the two detectors of FIG. 6.

The detectors 84, 86 provide input signals to an analogue amplifying and classification circuit shown in FIG. 8. Here the signals from both diodes are amplified using the different inputs of an operational amplifier 108, but the signals from detector 84 are subjected to pre-amplification by an operational amplifier 110 the gain of which is adjustable by altering the value of the feedback resistor 112.

The circuits of FIGS. 7 and 8 are set up using a sheet of white paper at 92. This gives rise to a dc signal from both 84, 86 and the value of 112 is adjusted to produce a zero output signal in the output of the third operational amplifier 114, with the white sheet in place.

Variable resistor 116 determines the threshold at which operational amplifier 114 changes state to produce a current for driving indicating LED 118, and the value of 116 is adjusted by replacing the white paper with a flat surface containing the OVM ink to which the device is to respond in use, and adjusting 116 until the LED illuminates.

Tests on a device constructed in accordance with FIGS. 6 to 8 using Hewlett-Packard HLMP-C515 and HLMP-215 LEDs and Texas Instruments TSL251 lensed photodiodes as items 82, 84 indicated that it could distinguish between OVM and non-OVM (and pearlescent) inks without error for ink samples 1, 3 and 12 of Table 1, and produced a "grey scale" output representing the concentration or quality of the OVM ink. The switching speed was governed by the response of the selected diodes 84, 86 but by selecting different photodiodes, this could be increased from 5 KHz in the circuits shown, to 1 MHz if desired.

An alternative device is shown in FIG. 9. This is essentially the same as the arrangement shown in FIG. 6 with the addition of a third photodiode 120 located midway between the other two photodiodes to allow signals at 90° from the incoming light from the LEDs to be interrogated by the third photodiode 120. The other items in the arrangement shown in FIG. 9 are identified by the same reference numerals as used in relation to FIG. 6 and the functionality of the devices is as described in relation to the earlier Figure.

The LEDs 82 and 84 in FIG. 9 may be driven by a switched power supply similar to that shown in FIG. 7 or the power supply shown in FIG. 10 in which the pulse generating circuit based on the 555 semiconductor device 100 is removed and pulses from a data acquisition card linked to a computer which operates to process the output signals, or from an analogue to digital converter, are supplied in place of the pulses from the device 100. Again the components in the remainder of the circuit of FIG. 10 are the same as those in FIG. 7 and the same reference numerals are used to denote the items concerned.

No detail is shown of the analogue to digital converter since this is a proprietary item and the preferred device is a Pico ADC-11, 10 channel, analogue to digital converter which can be obtained from RS Components under Part No. 830053.

A personal computer (not shown) can be used to control the switching of the two LEDs via the ADC.

Figure 11:
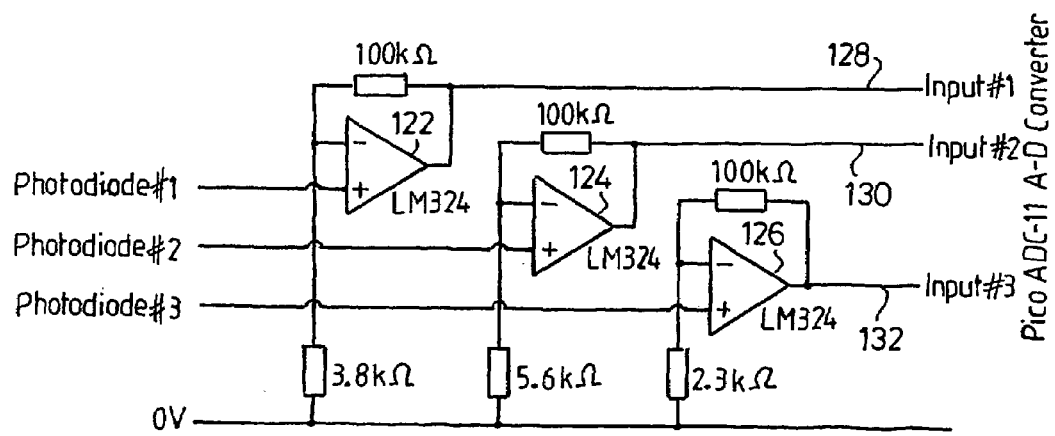
FIG. 11 is a schematic diagram of a signal processing circuit for amplifying analogue signals from the three detectors of FIG. 9, before conversion to digital signals for processing by the computer.

The voltage outputs from the three photodiodes 84, 86 and 120 provide inputs to three operational amplifiers 122, 124 and 126 shown in FIG. 11. Each includes a resistive feedback loop so that the gain of each can be adjusted to compensate for different output signal levels from the diodes. The outputs appear on lines 128, 130 and 132 which supply three inputs of the ADC-11 analogue to digital converter. The latter serves to digitise the analogue signals on lines 128, 130 and 132 to provide digital information to a computer (not shown) to enable the signals to be processed and analysed digitally, as well as providing synchronous LED switching signals for the LED control circuit of FIG. 10.

Figure 13:
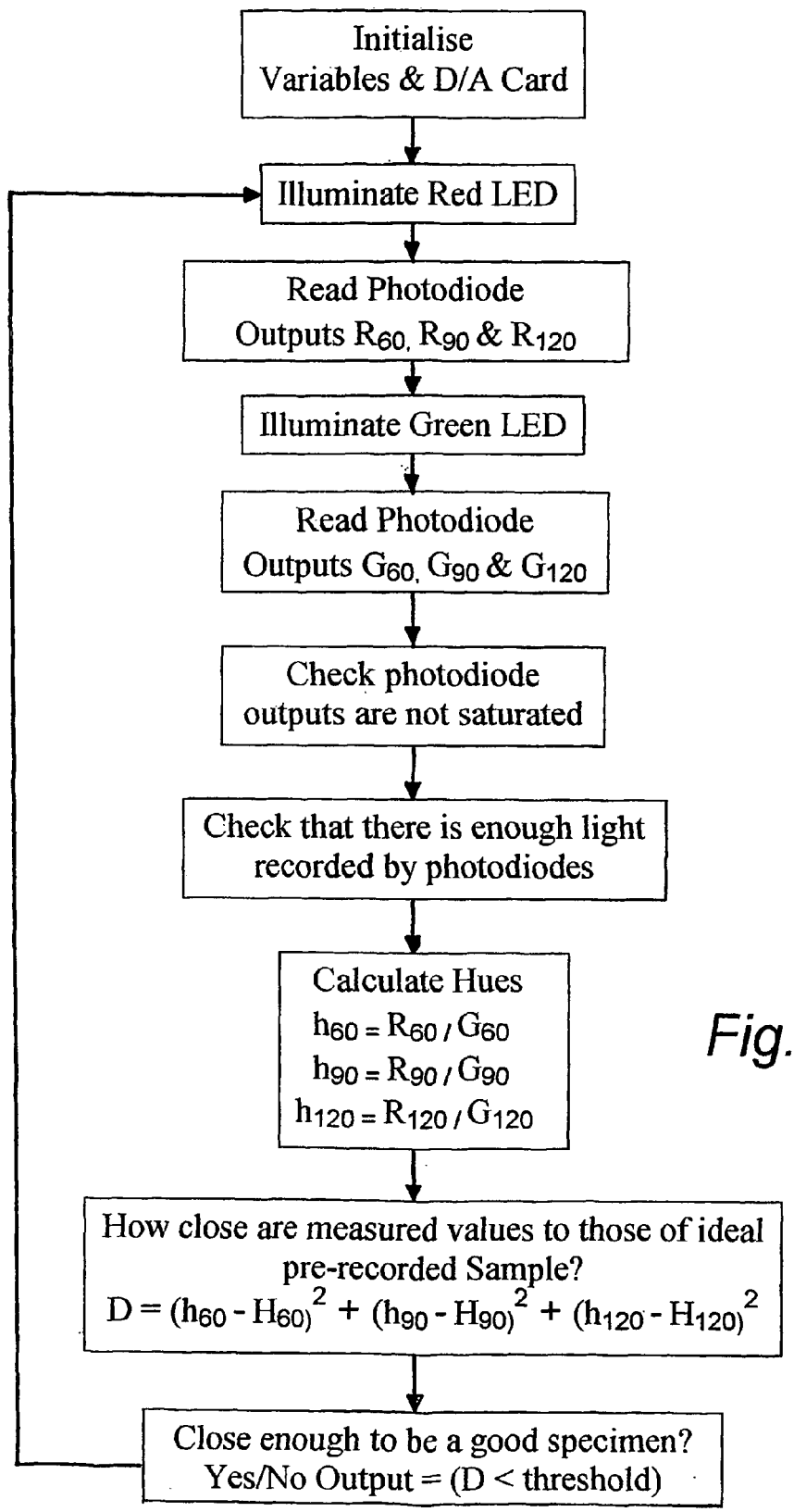
Figure 14:
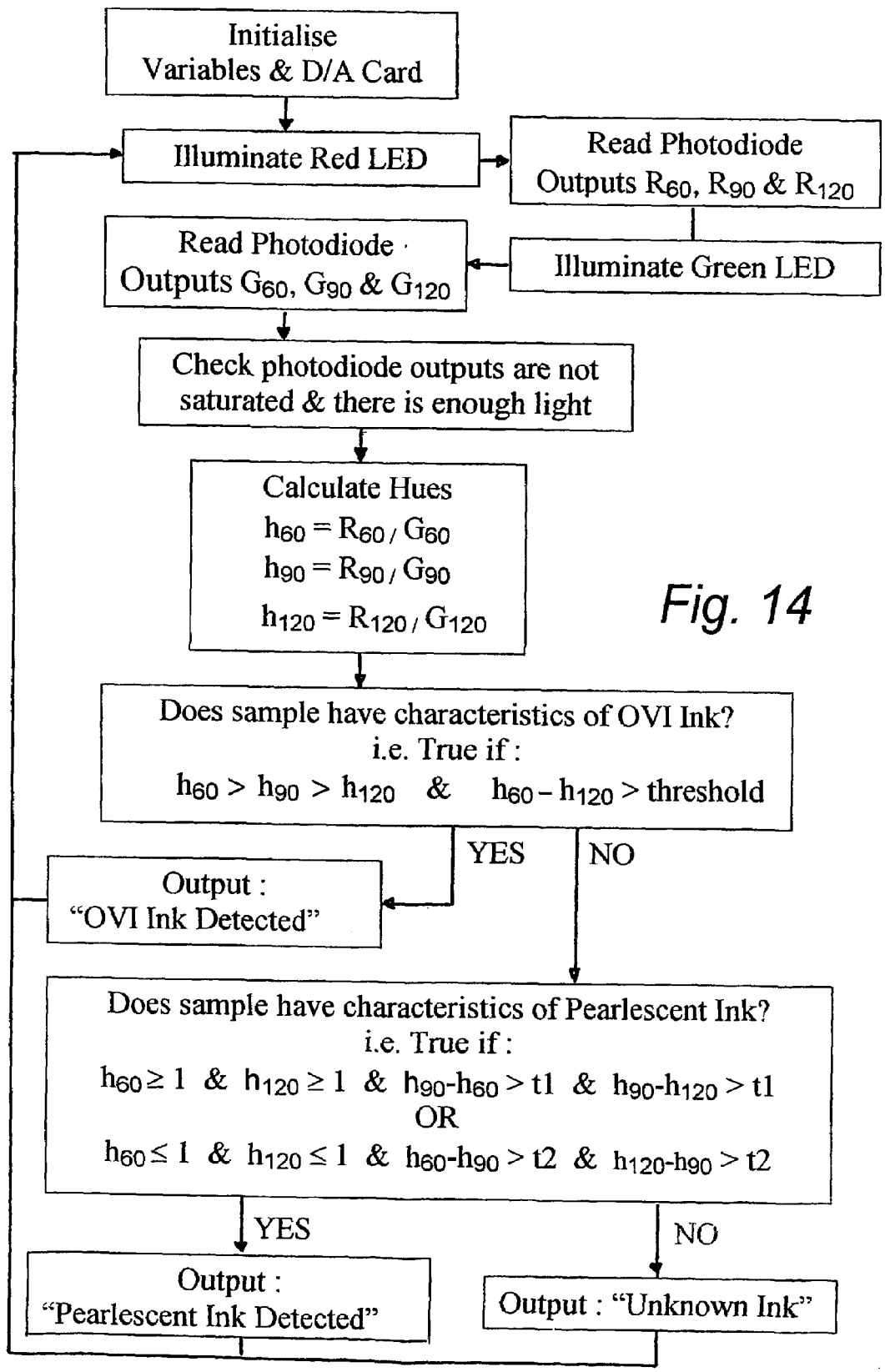

Three computer programs are set out in FIGS. 12, 13 and 14, each of which if run on a personal computer will analyse the digital data from the outputs 128, 130 and 132 to provide a classification of an ink printed or coated surface in the window 90.

The program shown in FIG. 12 only takes the data from lines 128 and 132 of FIG. 11 and ignores the 90° photodiode 120. The logic and processing replicates the operation of the circuit shown in FIG. 8 and provides an output which indicates that an OVM has been detected if an output signal is greater than some threshold.

The second program of FIG. 13 utilises all three photodiode signals and generates red/green ratios at each of three scattering angles.

Using this computer-based system, the sensor was able to identify samples 1, 2 and 3, 5, 7 and 11 from Table 1, for which the LED output of wavelengths were optimal, and misclassification was negligible.

The program of FIG. 13 allows a non-linear nearest neighbour classifier to be constructed which is optimal in the sense that it will identify the exact parameters that characterise a given ink. The resulting system is very ink specific and classifies an ink according to a given ink being present in exact quantities. Insofar as the device is to be used as a quality control device, this is no serious limitation and a classifier constructed using the computer program shown in FIG. 13 will provide just the sort of tool required to maintain high consistent quality of OVM printed surfaces.

The third program, of FIG. 14 broadly classifies a given ink as isotropic, pearlescent, OVM or non-pearlescent OVM. It can be seen from an analysis of the measure R-G ratios shown in Table 3 that printed inks (both OVM and non-OVM) fall into four general categories. The first two categories cover matt and glossy inks, and the latter two categories OVM and pearlescent inks. Matt inks appear to exhibit constant red-green ratios with scattering angle, whereas glossy inks exhibit a de-saturation of colour (that is the R-G ratio tends to unity) for specular reflection. On the other hand, OVM inks for which the sensor is optimised, exhibit a decrease in the R-G ratio with increased scattering angle, and these are always substantial. Finally the pearlescent inks for which the sensor is preferably optimised (namely for samples 5, 7 and 11) exhibit a saturation in colour, that is a divergence from unity of the R-G ratio, for specular reflection.

The non-linear classification strategy of the third computer program in FIG. 14 allows a broader classification according to ink type and an estimate of the quantity of ink present on the white substrate. This allows a broad classification of ink type and the best classification strategy is to be found by dividing the three-dimensional space constructed from the logarithm of the red-green signals at each of the scattering angles, into regions. In this way inks can be broadly classified as to type, and the distance from the centre of the region (which corresponds to white paper), provides an estimate of the amount of each ink present. This concept will be described later in more detail in relation to FIG. 19.

The very accurate ink identification characteristics of the second program (FIG. 13) and the broad classification characteristics of the third program (FIG. 14) mean that an overall classifier may require two channels, one operating the FIG. 13 program, and the other the FIG. 14 program, to allow overall classification and ink identification to be performed quickly and accurately.

Figure 15:
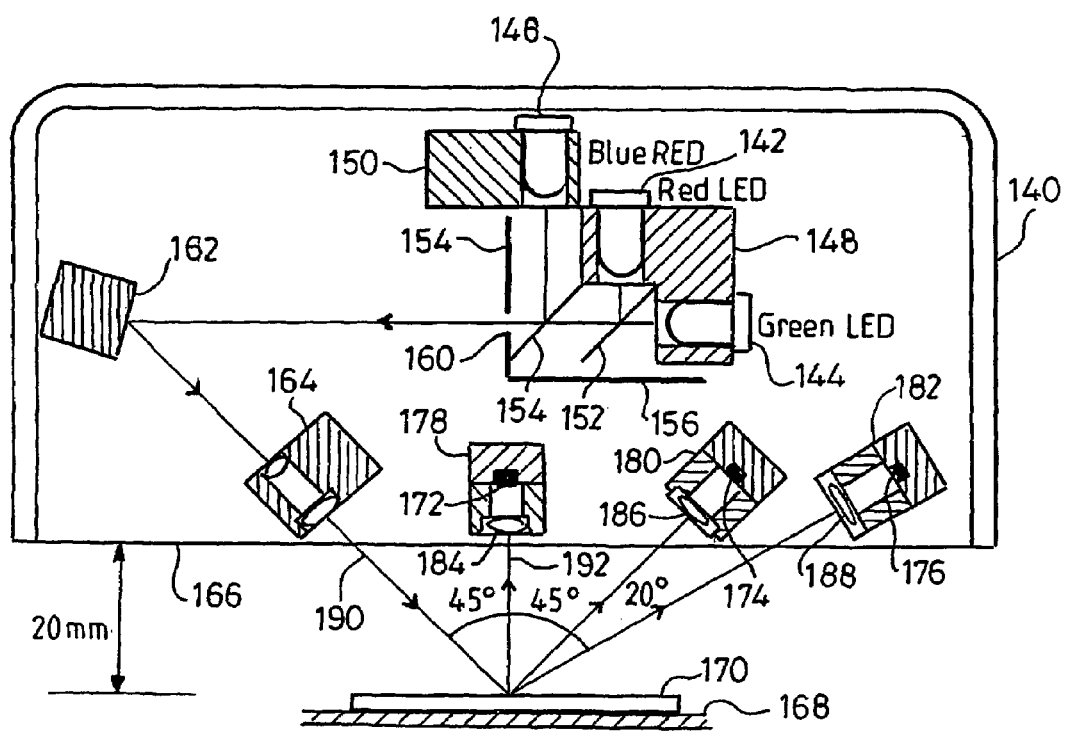
FIG. 15 is a layout diagram of an optical arrangement containing a viewing window, three LED light sources and three detectors, for determining the reflectance characteristics of a printed/coated surface in the viewing window, for use with an analogue acquisition card with a computer used for digital signal processing.

In FIG. 15 the photodiodes and LEDs are housed within a housing 140. Red and Green LEDs 142, 144 are mounted within a block 148 and a third Blue LED 146 is mounted within an adjacent block 150, to facilitate the mounting of the LEDs within the casing. The Red and Green axes are perpendicular and the axis of the Blue LED is parallel to the Red axis. Dichroic mirrors 152, 154 at 45° to the LED axes combine the light from the three LEDs into a single axis 158 (coaxial with the Green axis in the arrangement shown) and a sub assembly is formed using the two blocks 150, 152 and a thin walled box, two walls of which are denoted by 154, 156 which co-operate with the blocks and other side walls of the box to form an enclosure which traps all the light from the LEDs within the enclosure except light along the axis 158 which can pass out through an aperture 160 in the wall 154.

Escaping light is reflected by a mirror 162 mounted within the casing so a to project light through an imaging lens assembly 164 which can pass out of the casing through a window 166 in the underside thereof.

A platform 168 associated with the casing 140 and spaced from the window 166 by a predetermined distance serves as a support for a substrate 170 which carries in or on its upper surface a coating of an ink, dye or other material which may contain an OVM.

Three photo-detectors 172, 174, 176 are located within three housings 178, 180, 182 respectively which also house focusing lenses 184, 186 and 188 for focusing light reflected by the surface of the substrate 170, at 45°, 90° and 110° relative to the direction of the incident light 190 from the imaging lens assembly 164, along axes 192, 194 and 196.

The lens assembly 164 and the distance from the window 166 to the substrate surface 170 (typically 20 mm) are selected so that a small spot of light some 2 mm in diameter is formed on the substrate surface. The imaging lens assembly 164 preferably has a 5 mm aperture limiting the angular range of the illumination incident on the surface to ±10 degrees about the axis 190.

In general the angle between axis 190 and the normal to the substrate surface is selected to be 45°. This angle is expressed in this way, since the surface may not be entirely flat and may even be curved, but provided the region on which light from 164 is incident is flat over an area at least 2 mm in diameter, and the axis 190 is at 45° to the normal to that region of the surface, it is relatively unimportant if the remainder of the substrate is not coplanar therewith.

If checking the material in or on the same part of each of a plurality of similar substrates (e.g. similarly sized security documents such as banknotes) it is merely necessary for each document to replace the previous one in the same position relative to the window 166 on the platform 168.

If checking that a continuous length of sheet material has a required material in or on its surface as a result of a printing and/or coating treatment, it is merely necessary to move the sheet material relative to the window, whilst maintaining the region illuminated by the light from 164 at a constant distance from the window and in the correct plane.

In either event the three LEDs may be operated in rapid succession so that the substrate is successively illuminated by Red, Green and Blue light and the photodiodes are addressed at appropriate points in time corresponding to the three illumination intervals, so that the substrate surface and the three photodiodes are only presented with light of one wavelength during each illumination interval.

Where the substrate is replaced by another to be illuminated and evaluated in the same way, the LEDs and/or the photodiodes may be inhibited during the replacement.

Figure 16:
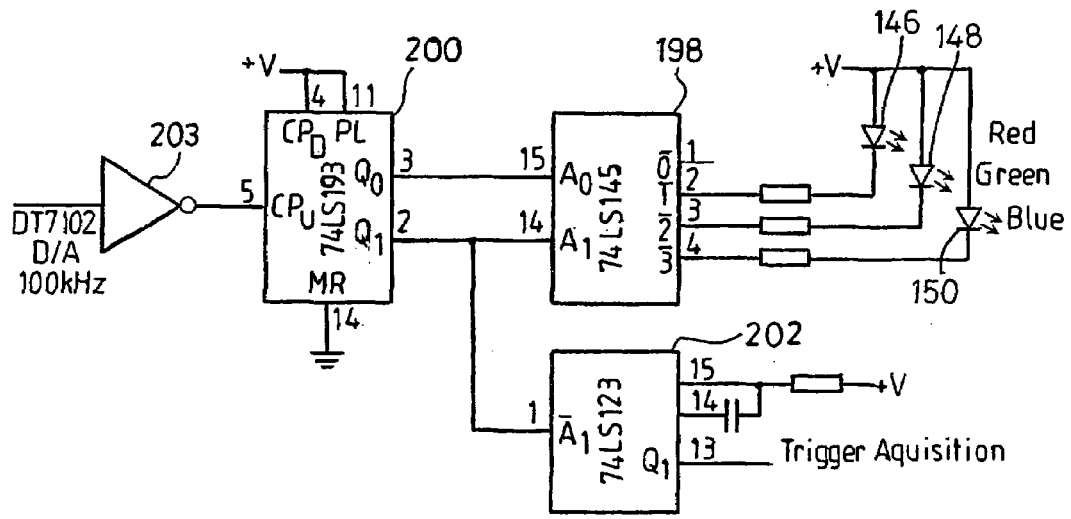
FIG. 16 is a schematic diagram of the control circuit for alternately powering the three LED sources of FIG. 9, using digital signals derived from an analogue acquisition card driven by the computer.

FIG. 16 shows how three LEDs 146, 148 150 are sequentially switched ON and OFF by current from pins 2, 3 and 4 of device 198 (a type 74LS145 counter). Pin 15 of 198 is connected to pin 3 (the $Q_o$ output) of device 200 (a type 74LS193 counter) pin 2 of which is connected to pin 14 of 198 and pin 1 of device 202 (a type 74LS123 device).

A 100 KHz signal is supplied from a data acquisition card type DT7102 (not shown) via an amplifier 203 to pin 5 of device 200. Pin 13 of 200 provides signals to the card DT7102 to control the reading of the output signals of the photodiodes 172, 174 and 176.

Successive illumination of the LEDs 146, 148 and 150 and the synchronous interrogation of the photodiodes 172, 174 and 176 is controlled by clock pulses derived from the 100 KHz signal. Since each transition of the 100 KHz signal can be used to generate a clock pulse, the latter will be generated at the rate of 200,000 per second. The illumination and interrogation process is performed by a succession of 16 clock pulses.

The first of the 16, pulse 1 causes pin 1 of 198 to go LOW and remain LOW for pulses 2–4. Pulses 2, 3 and 4 cause the outputs of photodiodes 172, 174 and 176 to be read and stored. Since pins 2, 3 and 4 of 198 remain HIGH during this time, all three LEDs remain off and the outputs from the photodiodes during pulses 2, 3 and 4 will correspond to background light reflected by the surface of 170 and received by each of the photodiodes.

The fifth of the 16 pulses causes pin 1 of 198 to go HIGH and pin 2 to go LOW and remain LOW for pulses 6, 7 and 8. As with pulses 2, 3 and 4, pulses 6, 7 and 8 cause photodiodes 172, 174 and 176 to be read in succession. Since pin 2 of 198 is LOW, the Red LED 146 will be illuminated, and during pulses 6–8 the output signals from 172, 174, 176 will correspond to Red light reflected from the surface of 170.

With the arrival of pulse 9, the LOW output of 198 transfers to pin 3 causing the Green LED 148 to illuminate, and during pulses 10, 11 and 12 the response of the photodiodes to reflected Green light from the surface 170 is read out.

With the arrival of pulse 13, the LOW output of 198 transfers to pin 4, causing the Blue LED 150 to illuminate and during pulses 14, 15 and 16 the response of the photo-detectors to reflected Blue light from the surface 170 is read out.

The process will repeat during each consecutive group of 16 clock pulses.

It has been found advantageous for pulses 1, 5, 9 and 13 to be redundant as far as read-out of the photodiodes is concerned, since although the LEDs switch ON and OFF instantaneously, there is a short rise time associated with photodiode operation and the short period of time between the arrival of pulses 5 and 6 (9 and 10, and 13 and 14), gives the photodiodes a chance to respond to the new light level incident thereon as each of the LEDs is turned on in turn. In this way the photodiodes will be in a steady-state condition when their output signals are read out.

Figure 17:
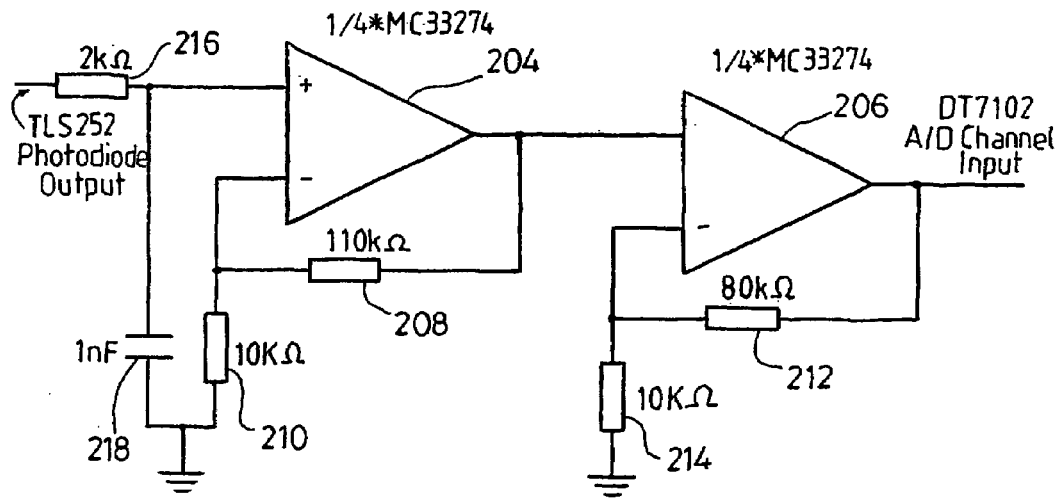
FIG. 17 is a schematic diagram of the amplifier circuit for the photodiodes prior to acquisition by a computer driven analogue acquisition card.

FIG. 17 shows one channel of a three channel signal amplifier for amplifying and shaping the signals from the photodiodes 172, 174 and 176. Two MC33274 quad op-amplifier devices 204, 206 are employed, one channel of each being left unused.

Corresponding amplifiers in each of 204, and 206 are connected in series with feedback via resistor networks 208, 210 and 212, 214 being applied to the inverting input signal of each amplifier. Adjustment of the values allows the signal gain of each channel to be varied, if necessary, to balance up the output signal levels from the photodiodes. An input resistor 216 and shunt capacitor 218 connects each photodiode to its respective amplifier input. Capacitor 218 is typically 1nF.

The amplified photodiode output signals are applied to three inputs of the multi-channel A/D convertr of the data acquisition board (not shown) type DT7102.

Suitable photodiodes are TSL 252.

The LEDs are selected to produce monochromatic light of 654 mm (Red), 574 mm (Green) and 472 mm (Blue). As described above they are flash-illuminated repetitively in a cycle.

The repetition rate of the cycle is 12.5 KHz if a clockpulse rate of 200 KHz is employed. This is software controlled by a computer via a data acquisition card producing a 100 kHz signal. The LEDs are chosen to give as good a match for as many optimal measurement wavelengths (as in Table 2) as possible.

Light scattered and reflected by the surface of 170 is collected simultaneously by the three photodiode units 178, 180 and 182 spaced at scattering angles of 45°, 90° and 110° from the LEDs, each of which is focused on the illuminated portion of the surface. The scattering angles of the photodiodes are chosen to be as close as possible to the optimal detector angles given above, given also the practical considerations of their physical size and mounting. The amplified voltages generated from the three photodiodes are converted to digital values using an acquisition card (not shown) after which the three output signal values can be stored in a computer (not shown).

The computer is then used to process the recorded data to determine whether a particular material is present in or on the surface, and whether or not it is in the required quantity. This is done using one of three programs, each subjecting the photo-detector output signal values to one of three different algorithms, thereby performing one of three different methods, detailed as follows:

Method I

This gives a simple linear measure of the quantity of a non-pearlescent OVM present on a substrate using just two LEDs and two of the photodiodes at scattering angles of 45° and 110°. The two LEDs used are chosen according to the properties of the OVM to be looked for, as detailed in Table 2. The method can only determine if the one material type is present on the substrate, and may be confounded if two or more OVMs are present. Using just the red and green LEDs to detect, say, ink Sample 1, the technique proceeds by calculating the value of M using the algorithm:

$$M=|(R_{110}-R_{45})-A*(G_{110}-G_{45})|$$

In a first calibration step, the photodiode amplifier gains are adjusted to compensate for any alignment differences, so that $R_{110}=R_{45}$.

The constant A can then be set. A is a constant that is adjusted to compensate for differences between the responses of the two photodiodes to the illumination wavelength. It is found by illuminating matt white paper, and adjusting the value of A until M is reduced to zero.

When a substrate printed with a non-pearlescent OVM ink is illuminated instead there will be a difference between the values of $(R_{110}-R_{45})$ and $A*(G_{110}-G_{45})$ giving rise to a non zero value for M. The magnitude of M for any given ink relates to the quantity of the ink on or in the substrate. Matt substrates (e.g. white paper, coloured card) do not produce these differences, giving rise instead to $R_{110}$ being very close to $R_{45}$ and $G_{110}$ being very close to $G_{45}$, thus resulting in a zero or near zero value, for M.

If the value of M is sufficiently greater than zero to indicate that the non-pearlescent OVM ink is present, the actual value of M can be compared with a threshold value t (found by experiment using different concentrations of the OVM concerned and observing values of M). A look-up table of values of M can be assembled from such data if desired, to provide indications of concentration in relation to measured values of M.

If the value of M is less than a particular value (i.e. is too close to zero) it is not necessarily true to assume that this corresponds to a very low concentration of the particular OVM, since this may indicate that no OVM is present and the actual value of M is merely due to errors, resulting in a non-zero value of M, when it should actually be zero.

Figure 18:
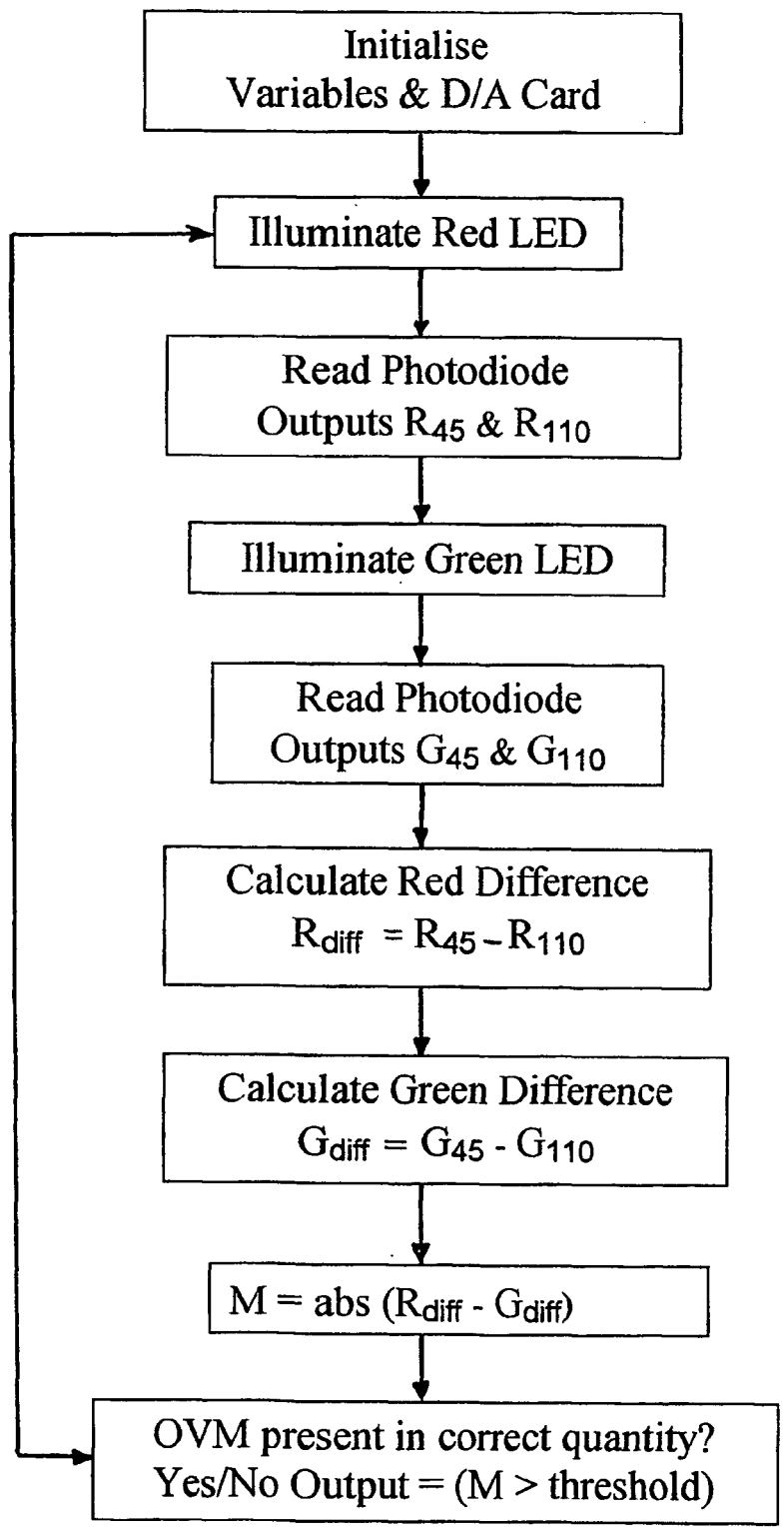
FIG. 18 is a flow chart of a computer program for implementing a first method (method I) to be described, FIGS. 19(a), (b) and (c) are graphical plots of log (hue) ratios from different pairs of detectors in the arrangement of FIG. 9—used to derive a logic table for use in a second method (method II) to be described.

A flow chart of the logic and decisions to be performed by a computer to determine whether a particular OVM is present is set out in FIG. 18.

This particular method has been described earlier, in relation to FIG. 6, where it has been shown that A/D conversion is not necessary, and simple analogue techniques may be employed to determine if the photo-detector output signals indicate if a particular OVM is present. The foregoing illustrates how a general purpose detector incorporating more LEDs and photodiodes than are actually necessary to perform Method I, using a Data acquisition card with A/D conversion and a computer, can also be used to perform the same method.

Method II

This method identifies OVM inks by examining the relationship of the ratio of one colour with respect to another reflected by a particular OVM ink, as a function of increasing amount of ink printed on or otherwise applied to a white substrate. It is also useful for discriminating between specific ink group types irrespective of the quantity of ink printed.

Although many combinations of LED illumination wavelengths are possible, measurements using just red and green LEDs but inspecting reflected light at three different angles, allows many of the samples in Table 2 to be differentiated between, using just two LEDs and three photodiodes.

Samples 8, 9 and 10 cannot be discriminated between using just red and green LEDs, but a similar technique utilising either red and blue, or blue and green LED combinations, allows these inks to be identified.

Figure 19A:
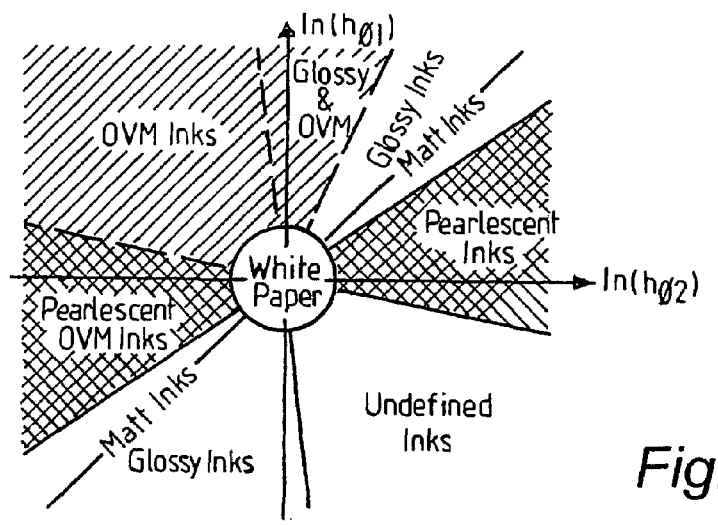
Figure 19B:
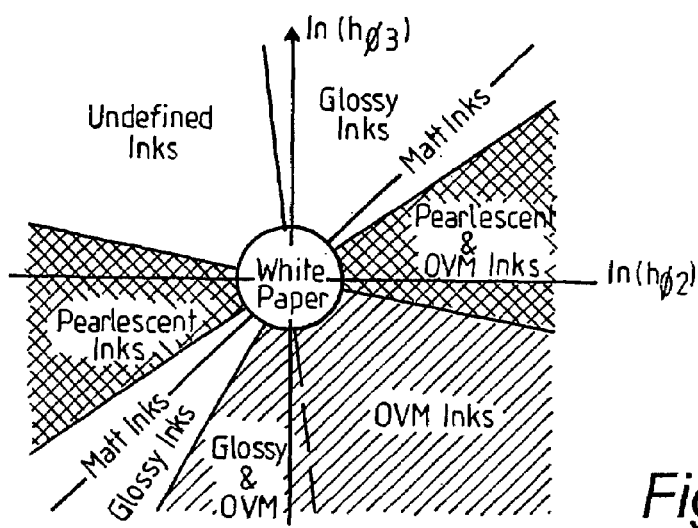
Figure 19C:
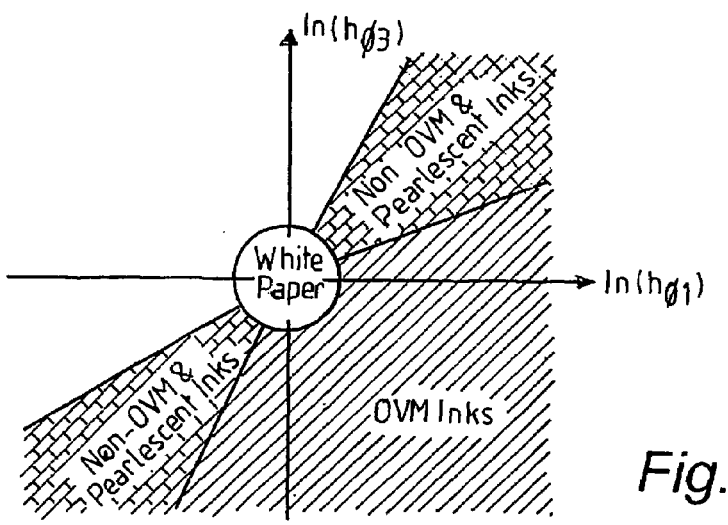

FIG. 19 shows graphs of logarithms computed for the red-green ratios (or hue values) themselves calculated for a wide variety of different ink samples detailed in Table 2. The red-green ratios (or hue values) $h_{\varnothing 1}$, $h_{\varnothing 2}$, $h_{\varnothing 3}$ are calculated after removing background light (measurements $D_{45}$, $D_{90}$ & $D_{110}$), as follows:

$$h_{\varnothing 1}=h_{45}=(R_{45}-D_{45})/(G_{45}-D_{45})$$

$$h_{\varnothing 2}=h_{90}=(R_{90}-D_{90})/(G_{90}-D_{90})$$

$$h_{\varnothing 3}=h_{110}=(R_{110}-D_{110})/(G_{110}-D_{110})$$

FIG. 20 is a schematic representation of the decision matrix of FIG. 19. This can be best understood by considering a system set up so that reflected Red light gives small $h_{\varnothing 1}$ $h_{\varnothing 2}$ and $h_{\varnothing 3}$ whereas reflected Green light gives larger values of $h_{\varnothing 1}$ $h_{\varnothing 2}$ and $h_{\varnothing 3}$.

For a non-pearlescent OVM, light leaving the surface at a low scatter angle will tend to look green, and will thus produce a high $h_{\varnothing 1}$ value whereas light at a larger scattering angle will tend to look Red and produce a low $h_{\varnothing 3}$.

Thus for such an OVM, $h_{\varnothing 1} > h_{\varnothing 3}$.

Specular reflection (somewhere between the two scattering angles considered above) will tend to be more Red than Green, so that $h_{\varnothing 2}$ will normally be between $h_{\varnothing 1}$ and $h_{\varnothing 3}$.

For a pearlescent OVM, light leaving the surface at large and small angles of scatter will tend to white, thus $h_{\varnothing 1}$ and $h_{\varnothing 3}$ will both tend to unity. However light due to specular reflection will posses more colour and $h_{\varnothing 2}$ will diverge from unity.

For example if the light reflected at high and low scatter angles is a very pale red (i.e. more white than red) the specular reflection will look very red and $h_{\varnothing 2}$ will be a small value<1.

Therefore in this case:

$$h_{\varnothing 2} < h_{\varnothing 1} \text{ and } h_{\varnothing 2} < h_{\varnothing 3},$$

where $h_{\varnothing 1}$ and $h_{\varnothing 3}$ both tend to be just less than unity.

In an alternative example where the reflected light at the high and low scatter angles is a very pale green (i.e. more white than green), $h_{\varnothing 1}$ and $h_{\varnothing 2}$ are again very close to unity (albeit this time slightly greater than unity), and the specular reflection will look very green, and the value of $h_{\varnothing 2}$ will be large—and certainly larger than $h_{\varnothing 1}$ and $h_{\varnothing 3}$.

Therefore in this case:

$h_{\emptyset 2} > h_{\emptyset 1}$ and $h_{\emptyset 2} > h_{\emptyset 3}$,

For a glossy ink, let us consider a system set up so that reflected Red light give small values for $h_{\emptyset 1}$, $h_{\emptyset 2}$ and $h_{\emptyset 3}$ whereas reflected Green light gives high values for $h_{\emptyset 1}$, $h_{\emptyset 2}$ and $h_{\emptyset 3}$.

Here a glossy Red ink will yield small values for $h_{\emptyset 1}$ and $h_{\emptyset 3}$ at large and small scatter angles whereas specular reflection will tend to look white, so that $h_{\emptyset 2}$ will be larger than both $h_{\emptyset 1}$ and $h_{\emptyset 3}$.

Conversely if the ink is a glossy Green ink, then it will look green at high and low scatter angles, so yielding larger values for $h_{\emptyset 1}$ and $h_{\emptyset 3}$ and specular reflection will tend to look white, so that $h_{\emptyset 2}$ will be smaller than both of $h_{\emptyset 1}$ and $h_{\emptyset 3}$.

Figure 21:
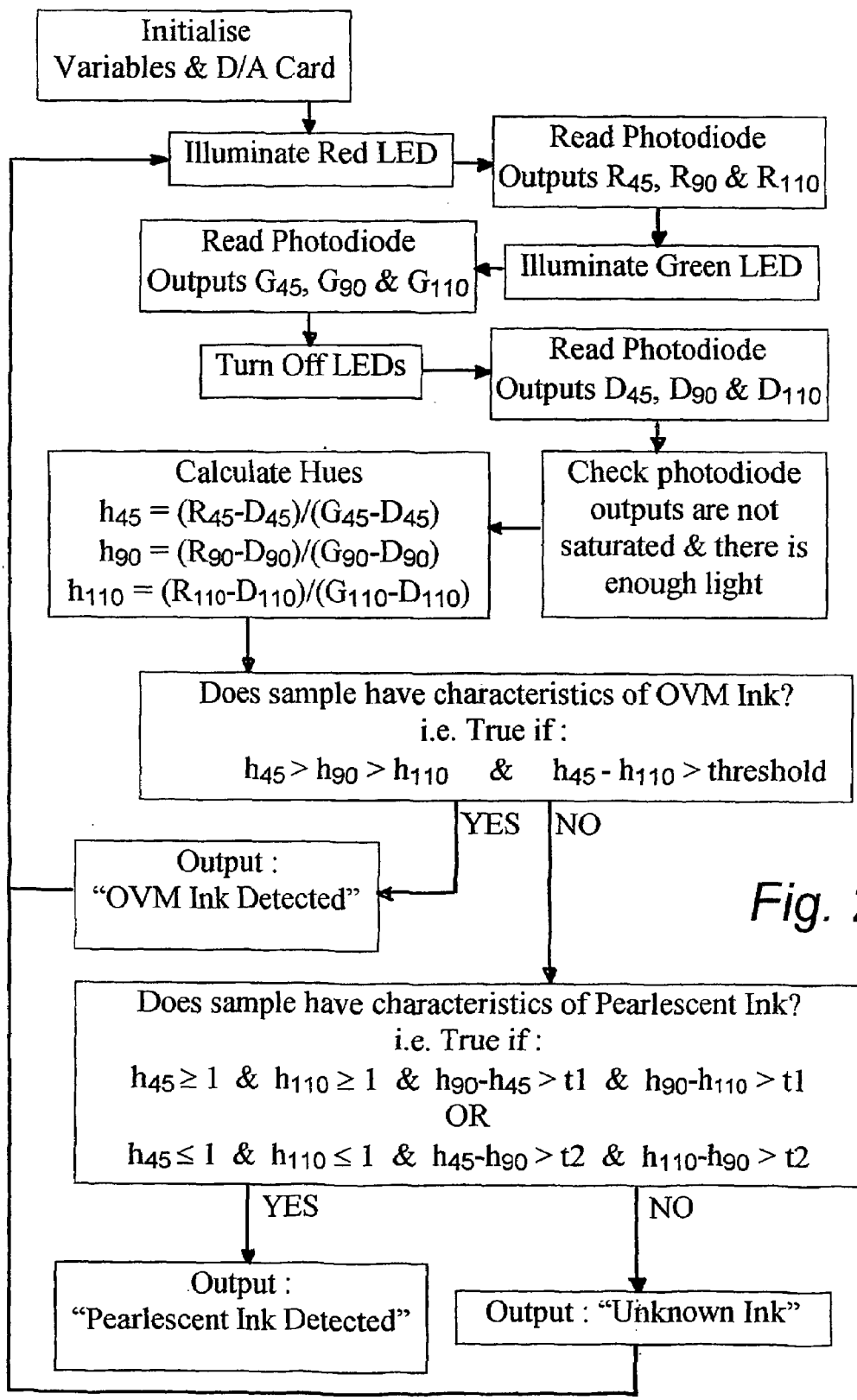
FIG. 21 is a command and logic diagram of a program for controlling a computer to implement method II.

A flow chart of the logic and decisions required to be performed by a computer to discriminate between non-pearlescent OVM, pearlescent OVM, and other inks is shown in FIG. 21.

A measure, Q, of the quantity of ink (i.e. concentration) in or on the white substrate, can be calculated using the values of $R_{45}$, $G_{45}$, $D_{45}$ etc. as follows:

$$Q = (\ln([R_{45} - D_{45}]/[G_{45} - D_{45}]) - 1)\wedge 2 +$$
$$(\ln([R_{90} - D_{90}]/[G_{90} - D_{90}]) - 1)\wedge 2 +$$
$$(\ln([R_{110} - D_{110}]/[G_{110} - D_{110}]) - 1)\wedge 2$$

Method III

This method is suitable for characterising and discriminating between several individual OVM inks provided the LED output wavelengths are selected for the particular individual inks. In fact the technique is not restricted to OVM inks and works equally as well with matt and glossy inks. It uses nearest neighbour classification, and may be confounded if the ink to be detected has not been printed in sufficient quantity. This latter problem can be overcome, at least in part by performing two or more classifying calculations in parallel for different ink quantities. Likewise alternative ink types can be detected more reliably by performing additional classifying calculations in parallel.

Figure 22:
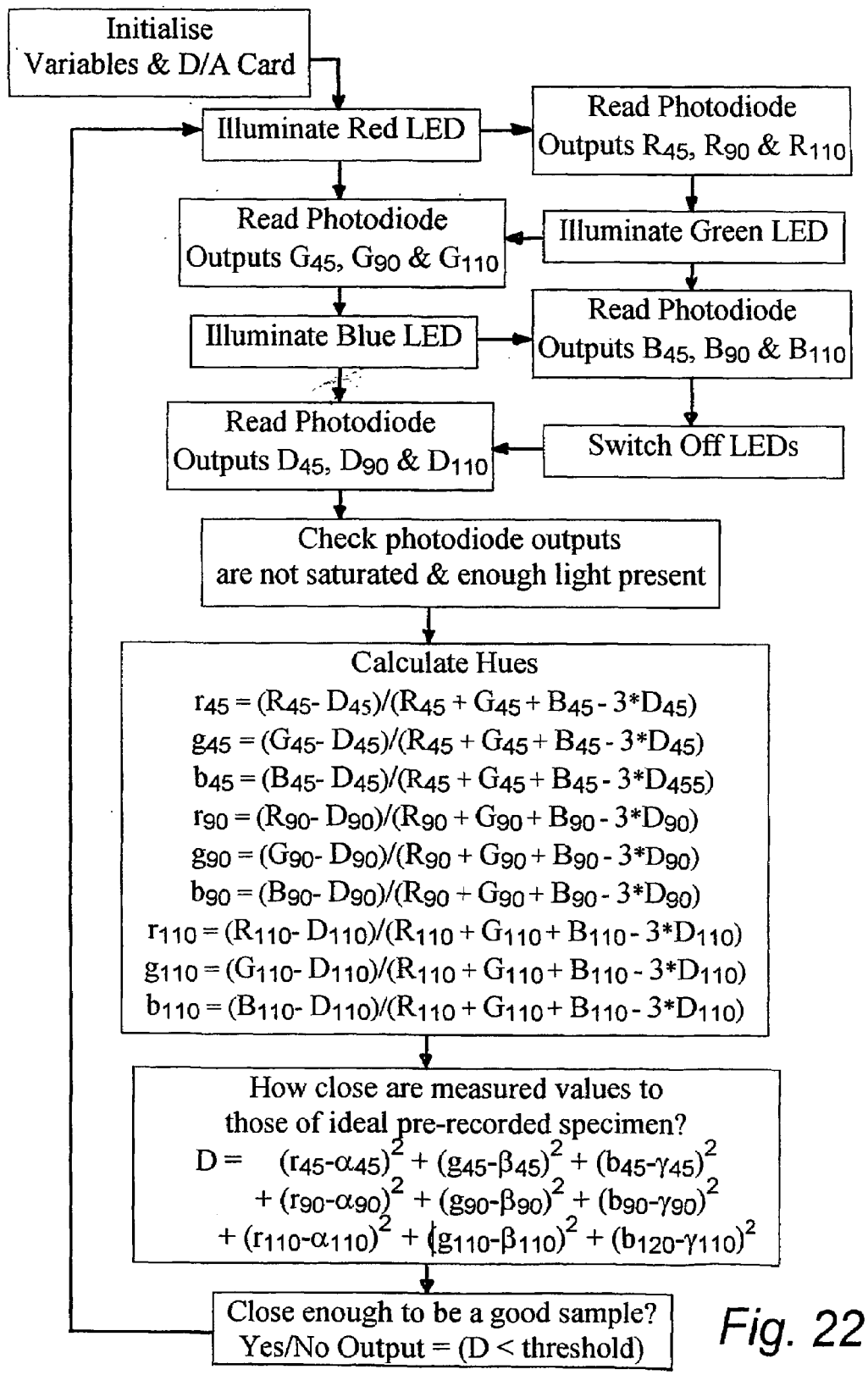
FIG. 22 is a command and logic diagram for controlling a computer to implement a third method (method III) to be described.

FIG. 22 lists the logic steps and decisions needed of a computer to classify one OVM ink printed at a particular density.

First the relative hues for each scatter angle are calculated from the recorded data after removing background light:

$r_{45} = (R_{45} - D_{45})/(R_{45} + G_{45} + B_{45} - 3*D_{45})$ $g_{45} = (G_{45} - D_{45})/(R_{45} + G_{45} + B_{45} - 3*D_{45})$ $b_{45} = (B_{45} - D_{45})/(R_{45} + G_{45} + B_{45} - 3*D_{45})$ $r_{90} = (R_{90} - D_{90})/(R_{90} + G_{90} + B_{90} - 3*D_{90})$ $g_{90} = (G_{90} - D_{90})/(R_{90} + G_{90} + B_{90} - 3*D_{90})$ $b_{90} = (B_{90} - D_{90})/(R_{90} + G_{90} + B_{90} - 3*D_{90})$ $r_{110} = (R_{110} - D_{110})/(R_{110} + G_{110} + B_{110} - 3*D_{110})$ $g_{110} = (G_{110} - D_{110})/(R_{110} + G_{110} + B_{110} - 3*D_{110})$ $b_{110} = (B_{110} - D_{110})/(R_{110} + G_{110} + B_{110} - 3*D_{110})$

These are then compared with relative hues from a pre-measured specimen sample of the ink identical to that desired to be detected. Assume that the pre-recorded hues of the specimen ink are denoted as $\alpha_{45}$, $\beta_{45}$, $\gamma_{45}$, $\alpha_{90}$, $\beta_{90}$, $\gamma_{90}$, $\alpha_{110}$, $\beta_{110}$, $\gamma_{110}$ for the hues of $r_{45}$, $g_{45}$, $b_{45}$, $r_{90}$, $g_{90}$, $b_{90}$, $r_{110}$, $g_{110}$ and $b_{110}$ respectively. The comparison is achieved using a nearest neighbour classifier according to vector distance mathematics. Put simply the value of N is computed using the following equation:

$$N = (r_{45} - \alpha_{45})^2 + (g_{45} - \beta_{45})^2 + (b_{45} - \gamma_{45})^2 +$$
$$(r_{90} - \alpha_{90})^2 + (g_{90} - \beta_{90})^2 + (b_{90} - \gamma_{90})^2 +$$
$$(r_{110} - \alpha_{110})^2 + (g_{110} - \beta_{110})^2 + (b_{110} - \gamma_{110})^2$$

If the calculated value of N is below a certain threshold L, that is N<L, then it can be said that the desired OVM ink has been detected and exists on the substrate in the correct quantity (density). Different ink quantities, or qualities, or types can be looked for simultaneously using different data sets of values for $\alpha_{45}$, $\beta_{45}$, $\gamma_{45}$, $\alpha_{90}$, $\beta_{90}$, $\gamma_{90}$, $\alpha_{110}$, $\beta_{110}$ and $\gamma_{110}$ pre-measured from appropriate specimens.

The methods and apparatus described herein may be employed for article authentication, quality control of sheet material having and OVM applied to its surface, and to document sorting.

Thus a method of article authentication wherein genuine articles are coated over at least part of their surface with a known OVM comprises the step of illuminating an article in accordance with any of the methods claimed herein and selecting the scattering and photo-detector angles and the wavelengths of the illuminating light in accordance with the OVM which should be on the article, and comparing the output signal value produced by the method against a look-up table (having at least one value therein) to generate an authentication or rejection signal depending on the value of the output signal.

Such a method can be used to authenticate a passport, and ID card, a driving licence, a banknote, a bond, a share certificate, a postage stamp, or any other security document.

Thus a method of checking the quality of the printing or coating of at least part of a substrate surface so as to deposit a particular OVM thereon comprises the step of illuminating the part of the surface which has been printed or coated with the OVM and investigating the reflected light in accordance with a method as claimed in any of claims 18 to 103 and generating a pass or fail signal depending on the value of the output signal generated by the method.

The printed substrate can be sheet material which has been or is being, or will be printed, to form one or more security documents.

The security documents may be banknotes in which the OVM is applied to some or all of the surface of the sheet material before during or after it is printed to create the banknotes.

Apparatus adapted to print or coat a specific OVM to sheet material may be combined with apparatus as described herein adapted to generate a pass or fail signal depending on the value of the output signal produced by the apparatus as printed or coated sheet material moves relative thereto.

Document sorting apparatus for sorting documents according to whether a particular OVM is in or on the surface of the document may be combined with apparatus as described herein adapted to generate a first control signal if the value of the output signal generated by the apparatus for a specific document indicates the particular OVM is present thereon and a second control signal if the output signal indicates no OVM to be present, and supplying a route controlling signal to the routeing apparatus to route the specific document to one of two destinations depending on whether a first or second control signal is generated by the apparatus.

TABLE 1

General visual properties of sample inks.

| Sample Number | Hue Observed at Various Viewing Angles | | |
|---|---|---|---|
| | Back Scatter | Specular | Glancing |
| 1 | Purple | Orange | Green |
| 2 | Orange/Pink | Green | Blue |
| 3 | Purple | Orange | Green |
| 4 | Gold | Gold | Gold |
| 5 | White | Light Green | White |
| 6 | White | Pink | White |
| 7 | Silver | Gold | Silver |
| 8 | White | Light Violet | White |
| 9 | Light Green | Light Red | Light Green |
| 10 | Light Yellow | Light Violet | Light Yellow |
| 11 | Light Pink | Apple Green | Light Pink |
| 12 | Purple | Orange/Green | Green |

TABLE 2

Optimal detector angles for 45° incident beam and

| Sample Number | Ink Type | Optimal Detection Angles $\theta_5$ | Best Wavelength |
|---|---|---|---|
| 1 | OV | 0°, 135° | 550 nm, 650 nm |
| 2 | OV | 0°, 135° | 520 nm, 600 nm |
| 3 | OV | 0°, 135° | 560 nm, 660 nm |
| 4 | (Metallic) | — | — |
| 5 | Pearlescent | 0°/135° & 90° | 500 nm, 700 nm |
| 6 | Pearlescent | 0°/135° & 90° | 525 nm, 640 nm |
| 7 | Pearlescent | 0°/135° & 90° | 525 nm, 650 nm |
| 8 | Pearlescent | 0°/135° & 90° | 460 nm, 600 nm |
| 9 | Pearlescent | 0°/135° & 90° | 510 nm, 700 nm |
| 10 | Pearlescent | 0°/135° & 90° | 460 nm, 580 nm |
| 11 | Pearlescent | 0°/135° & 90° | 500 nm, 700 nm |
| 12 | OV | 0°, 135° | 550 nm, 650 nm |

TABLE 3

Hue ratios measured by the computerised sensor for different inks.

| Paper Type | $h_{45}$ | $h_{90}$ | $h_{110}$ |
|---|---|---|---|
| White copy paper (matt) | 1.0220 (±0.0106) | 1.0351 (±0.0127) | 1.0331 (±0.0098) |
| Sketch pad paper (matt) | 1.0410 (±0.0097) | 1.0396 (±0.0081) | 1.0644 (±0.0091) |
| Pink calendar card (matt) | 1.2733 (±0.0048) | 1.2401 (±0.0133) | 1.1958 (±0.0178) |
| Yellow calendar card (matt) | 1.0636 (±0.0059) | 1.0350 (±0.0071) | 1.0261 (±0.0110) |
| Orange calendar card (matt) | 1.7290 (±0.0139) | 1.5196 (±0.0142) | 1.5186 (±0.0246) |
| Beige calendar card (matt) | 1.0095 (±0.0037) | 1.0121 (±0.0077) | 1.0164 (±0.0112) |
| Grey calendar card (matt) | 1.0058 (±0.0044) | 0.9811 (±0.0079) | 0.9617 (±0.0166) |
| Light blue card (matt) | 0.9348 (±0.0013) | 0.9519 (±0.0036) | 0.9565 (±0.0052) |
| Light green card (matt) | 0.9464 (±0.0043) | 0.9738 (±0.0046) | 0.9843 (±0.0049) |
| Dark blue folder card (matt) | 0.9563 (±0.0133) | 0.9281 (±0.0109) | 1.0577 (±0.0142) |
| Green folder card (matt) | 0.9510 (±0.0081) | 0.9492 (±0.0087) | 0.9660 (±0.0095) |
| Brown folder card (matt) | 1.1789 (±0.0116) | 1.1125 (±0.0035) | 1.1142 (±0.0124) |
| Yellow pages paper (matt) | 1.0841 (±0.0248) | 1.0494 (±0.0306) | 1.0566 (±0.0291) |
| News paper white (matt) | 1.0179 (±0.0282) | 0.9972 (±0.0218) | 1.0204 (±0.0280) |
| Envelope brown (matt) | 1.1232 (±0.0067) | 1.0581 (±0.0190) | 1.1086 (±0.0065) |
| Maroon thesis cover (matt) | 3.6571 (±0.0226) | 2.6571 (±0.0485) | 2.7122 (±0.0214) |
| Light red book cover (glossy) | 3.5824 (±0.0341) | 1.7056 (±0.1111) | 3.3564 (±0.1539) |
| Dark green book cover (glossy) | 0.5479 (±0.0131) | 0.7087 (±0.2240) | 0.7391 (±0.0559) |
| Syquest blue cover (glossy) | 1.0000 (±0.0367) | 1.0418 (±0.0132) | 1.1304 (±0.0814) |
| Light green RS cover (glossy) | 0.5000 (±0.0058) | 0.8775 (±0.1852) | 0.7179 (±0.0491) |
| Yellow pages cover (glossy) | 1.0128 (±0.0128) | 0.9191 (±0.0353) | 1.0391 (±0.0162) |
| Aluminium casing (brushed) | 0.9662 (±0.0124) | 0.9149 (±0.0164) | 1.0333 (±0.0134) |
| Beige computer casing (glossy) | 0.9752 (±0.0100) | 0.9416 (±0.0256) | 0.9905 (±0.0127) |
| Dark blue book (glossy) | 1.0909 (±0.0719) | 0.8426 (±0.0457) | 1.0513 (±0.0443) |
| Red RS cover (glossy) | 6.8876 (±0.1043) | 1.7767 (±0.0990) | 6.6304 (±0.2472) |
| Blue RS cover (glossy) | 0.5966 (±0.0109) | 0.9888 (±0.0583) | 0.6552 (±0.0287) |
| White book (glossy) | 0.9925 (±0.0049) | 1.0205 (±0.0160) | 1.0000 (±0.0034) |
| Bright red glossy leaflet (glossy) | 4.4338 (±0.1149) | 1.7085 (±0.0627) | 4.1333 (±0.1317) |
| Sample #1 (OVM) | 1.7432 (±0.0354) | 0.8049 (±0.0215) | 0.6916 (±0.0205) |
| Sample #2 (OVM) | 0.6244 (±0.0108) | 0.4919 (±0.0110) | 0.6801 (±0.0154) |
| Sample #3 (OVM) | 1.8609 (±0.0425) | 0.7646 (±0.0228) | 0.6472 (±0.0167) |
| Sample #4 (Metallic paint) | 1.2685 (±0.0238) | 1.0945 (±0.0309) | 1.3196 (±0.0320) |
| Sample #5 (Pearlescent ink) | 1.0458 (±0.0104) | 0.8622 (±0.0127) | 0.9492 (±0.0120) |
| Sample #6 (Pearlescent ink) | 1.0690 (±0.0136) | 1.0349 (±0.0130) | 1.0562 (±0.0142) |
| Sample #7 (Pearlescent ink) | 1.0465 (±0.0114) | 0.8832 (±0.8832) | 0.9994 (±0.0170) |
| Sample #8 (Pearlescent ink) | 1.0260 (±0.0077) | 1.0450 (±0.0127) | 1.0897 (±0.0111) |
| Sample #9 (Pearlescent ink) | 1.0181 (±0.0106) | 1.0325 (±0.0259) | 1.0864 (±0.0154) |
| Sample #10 (Pearlescent ink) | 1.0024 (±0.0090) | 0.9907 (±0.0266) | 1.0543 (±0.0171) |

TABLE 3-continued

Hue ratios measured by the computerised sensor for different inks.

| Paper Type | $h_{45}$ | $h_{90}$ | $h_{110}$ |
| --- | --- | --- | --- |
| Sample #11 (Pearlescent ink) | 0.9759 (±0.0095) | 0.7457 (±0.0152) | 0.9062 (±0.0121) |
| Sample #12 (Banknote OVM) | 1.2573 (±0.0428) | 0.8908 (±0.0168) | 0.8872 (±0.0259) |
| | (Standard deviations in brackets) | | |

The invention claimed is:

1. A method of determining if a surface contains a specific OVM comprising the steps of:
   (1) illuminating the surface using light containing two substantially monochromatic components of wavelength $\lambda_1$ and $\lambda_2$,
   (2) detecting the intensity of scattered light from the surface at two scattering angles $\varnothing_1$ and $\varnothing_2$ selected according to the OVM of interest,
   (3) computing the magnitude of the difference between the intensity values for $\lambda_1$ light at $\varnothing_1$ and $\varnothing_2$ less the difference between the intensity values for $\lambda_2$ light at $\varnothing_1$ and $\varnothing_2$, and
   (4) generating an output signal indicating the presence or absence of the specific OVM depending on the computed difference magnitude relative to a predetermined value,
   wherein the surface is illuminated separately first with monochromatic light of one wavelength and then with monochromatic light of the other wavelength, and wherein detection is performed by a single detector which is moved between two positions so as to receive light reflected/scattered from the surface first at one and then the other of the two angles $\varnothing_1$ and $\varnothing_2$.

2. A method as claimed in claim 1, wherein the computed difference magnitude is compared with a predetermined value to generate a first output signal value indicating the presence of the specific OVM, if the computed magnitude is at least as great as the predetermined value, or a second output signal value indicating that the specific OVM has not been detected, if the computed magnitude is less than the predetermined value.

3. A method as claimed in claim 1, wherein the surface is illuminated by the two monochromatic components simultaneously.

4. A method as claimed in claim 1, wherein detection is performed by means of two detectors which are positioned so as to receive light from the surface along the directions dictated by $\varnothing_1$ and $\varnothing_2$.

5. A method as claimed in claim 1, which includes the step of modifying the values of signals from the one detector by signal amplification of the detector output signals at the two different positions to take account of any inherent differences in intensity of the originating illuminations incident on the surface due for example to different intensity levels and/or any misalignment of the sources of the $\lambda_1$ and $\lambda_2$ light.

6. A method as claimed in claim 4, wherein the values of the signals from one or both detectors is modified by signal amplification to take account of any inherent differences in the responses of the two detectors to light of given intensity incident thereon, and any misalignment of the detectors.

7. A method of determining if a surface contains a specific OVM comprising the steps of:
   (1) illuminating the surface using light containing two substantially monochromatic components of wavelength $\lambda_1$ and $\lambda_2$,
   (2) detecting the intensity of scattered light from the surface at two scattering angles $\varnothing_1$ $\varnothing_2$ selected according to the OVM of interest,
   (3) computing the magnitude of the difference between the intensity values for $\lambda_1$ light at $\varnothing_1$ and $\varnothing_2$ less the difference between the intensity values for $\lambda_2$ light at $\varnothing_1$ and $\varnothing_2$, and
   (4) generating an output signal indicating the presence or absence of the specific OVM depending on the computed difference magnitude relative to a predetermined value,
   and including a calibration procedure in which the light is projected towards and the reflected/scattered light is received from, a non OVM containing matt white surface.

8. A method of determining if a surface contains a specific OVM comprising the steps of:
   (1) illuminating the surface using light containing two substantially monochromatic components of wavelength $\lambda_1$ and $\lambda_2$,
   (2) detecting the intensity of scattered light from the surface at two scattering angles $\varnothing_1$ and $\varnothing_2$ selected according to the OVM of interest,
   (3) computing the magnitude of the difference between the intensity values for $\lambda_1$ light at $\varnothing_1$ and $\varnothing_2$ less the difference between the intensity values for $\lambda_2$ light at $\varnothing_1$ and $\varnothing_2$, and
   (4) generating an output signal indicating the presence or absence of the specific OVM depending on the computed difference magnitude relative to a predetermined value,
   and in which the absolute value of the computed difference is compared with a range of possible values, the different values in the range corresponding to differing concentrations of the specific OVM in or on the surface under test.

9. A method as claimed in claim 1, wherein the light projected onto the surface is collimated.

10. A method as claimed in claim 4, wherein the signals from each detector are gated or addressed in synchronism with the changing wavelength of the illuminating light, so that during each gating or addressing period the wavelength of the incident light is known and there is no light of the other wavelength present to confuse matters.

11. A method of determining if a surface contains a specific OVM comprising the steps of:
   (1) illuminating the surface using light containing two substantially monochromatic components of wavelength $\lambda_1$ and $\lambda_2$,
   (2) detecting the intensity of scattered light from the surface at two scattering angles $\varnothing_1$ $\varnothing_2$ selected according to the OVM of interest, (3) computing the magnitude of the difference between the intensity values for $\lambda_1$ light at $\varnothing_1$ and $\varnothing_2$ less the difference between the intensity values for $\lambda_2$ light at $\varnothing_1$ and $\varnothing_2$, and (4) generating an output signal indicating the presence or absence of the specific OVM depending on the computed difference magnitude relative to a predetermined value, and wherein the difference magnitude M is computed in a way which compensates for variations in intensity between one wavelength component and the other, variations due to misalignment, and variations between detector responses, using the following equation:

$$M=|(K_1R_1-K_2R_2)-A*(K_1G_1-K_2G_2)|$$

where R and G represent the reflectance signal intensity values outputted by the photo-detectors at the illuminations of $\lambda_1$ and $\lambda_2$ respectively, the subscripts of R and G denoting measurements made by the two photo-detectors at the scattering angles of $\varnothing_1$ and $\varnothing_2$, and $K_1$ and $K_2$ are calibration constants to allow for misalignment and differences in the detector responses at $\varnothing_1$ and $\varnothing_2$ scattering angles, and A is a scalar constant which normalises the detector responses and alignment relative to the $\lambda_1$ and $\lambda_2$ illuminations.

12. A method as claimed in claim 11, wherein the calibration constants $K_1$ and $K_2$ are set by adjusting the gain of the detector output signal amplification.

13. A method as claimed in claim 11, wherein generation of a YES/NO output signal is achieved by comparing the computed value of M with a predetermined value T, itself derived by computing M from a surface containing a known minimum concentration of the OVM of interest.

14. A method as claimed in claim 11 further comprising the step of determining the value of M for each of a plurality of samples each containing the same OVM but at different concentrations per unit area, and storing same as a range of values of T, for comparison with computed values of M from surfaces having an unknown concentration of the OVM thereon.

15. A method as claimed in claim 11 in which calibrating the detector involves the steps of inserting a plain matt white surface in place of the surface to be tested, and adjusting the values of $K_1$ and $K_2$ so that $K_1R_1=K_2R_2=1$, and adjusting scalar A to give M=0.

16. A method as claimed in claim 15 comprising the steps of substituting the white surface with a sample having a printed or coated surface, and checking for the presence of the specific OVM, by comparing the computed magnitude of M with the predetermined threshold value T, and generating a YES output signal if the magnitude of M is equal to or greater than T and a NO output signal if the magnitude of M is less than the threshold T.

17. A method as claimed in claim 11 further comprising the steps of storing different values of T corresponding to different known OVM, for use with different combinations of $\lambda_1$, $\lambda_2$, $\varnothing_1$, and $\varnothing_2$, each unique to a particular OVM.

18. Apparatus by which an output signal is generated indicative of the presence of a specific OVM in or on a surface under test comprising:

1. a light source which produces and projects along a projection axis monochromatic light at each of two wavelengths $\lambda_1$ and $\lambda_2$ selected according to the specific OVM of interest;
2. means for locating the surface under test to receive the light with the projection axis at a specific angle to the surface;
3. two photodetectors, the first of which is located to receive light reflected at a first scattering angle $\varnothing_1$, and the second of which is located so as to receive light reflected at a second scattering angle $\varnothing_2$, from the surface, each photodetector producing an analogue signal indicative of the intensity of light incident thereon;
4. means for amplifying the signals from the photodetectors;
5. means for computing the value of the magnitude of the difference between the amplified intensity values for $\lambda_1$ light reflected/scattered from the surface at $\varnothing_1$ and $\varnothing_2$ less the difference between the amplified intensity values for $\lambda_2$ light at $\varnothing_1$ and $\varnothing_2$;
6. means for generating an output signal dependent on the magnitude of the computed difference value to indicate the presence of the material on the surface, and wherein the illumination intensities and/or the gains of the amplifying means are adjusted to calibrate the apparatus, during a calibration step.

19. Apparatus by which an output signal is generated indicative of the presence of a specific OVM in or on a surface under test comprising:

1. a light source which produces and projects along a projection axis monochromatic light at each of two wavelengths $\lambda_1$ and $\lambda_2$ selected according to the specific OVM of interest;
2. means for locating the surface under test to receive the light with the projection axis at a specific angle to the surface;
3. two photodetectors, the first of which is located to receive light reflected at a first scattering angle $\varnothing_1$, and the second of which is located so as to receive light reflected at a second scattering angle $\varnothing_2$, from the surface, each photodetector producing an analogue signal indicative of the intensity of light incident thereon;
4. means for amplifying the signals from the photodetectors;
5. means for computing the value of the magnitude of the difference between the amplified intensity values for $\lambda 1$ light reflected/scattered from the surface at $\varnothing_1$ and $\varnothing_2$ less the difference between the amplified intensity values for $\lambda_2$ light at $\varnothing_1$ and $\varnothing_2$;
6. means for generating an output signal dependent on the magnitude of the computed difference value to indicate the presence of the material on the surface.

and, wherein the light source comprises a pair of LED's, one of which emits near monochromatic light at or near $\lambda_1$ and the other of which emits near monochromatic light at or near $\lambda_2$, and the light from the two LED's is projected along a common axis.

20. Apparatus as claimed in claim 18 wherein the angle of incidence of the light upon the surface is at or close to 45 degrees.

21. Apparatus as claimed in claim 18 further comprising collimating means by which the projected light is collimated.

22. Apparatus as claimed in claim 18 wherein the photodetector means comprises a pair of photo-diodes.

23. Apparatus as claimed in claim 22 wherein each photo-detector is associated with a lens for focusing light onto the diode.

24. Apparatus as claimed in claim 23 wherein the lens has an aperture which is optimised to limit the angular range of scattered light incident on the detector, but allows appropriate and practicable levels of light through to the photodetector.

25. Apparatus as claimed in claims 19 further comprising a pulsed power supply for powering the two LED's such that the two LED's are operated alternately.

26. Apparatus as claimed in claim 25 wherein the repetition rate of the two LED's is greater than 1 KHz.

27. Apparatus as claimed in claim 26 wherein the repetition rate is less than 1 MHz.

28. Apparatus as claimed in claim 18 wherein the apparatus and computing means are electronically hard wired, or the detector means supplies signals to, and is controlled by, a computer with a suitable interface and data acquisition card.

29. Apparatus as claimed in claim 18 comprising analogue signal amplifying means and an analogue to digital converter (ADC) for supplying digital signals to the computing means.

30. Apparatus as claimed in claim 29 wherein the analogue signal amplifying means and the ADC are provided on the interface or on the data acquisition card or in the apparatus.

31. Apparatus by which an output signal is generated indicative of the presence of a specific OVM in or on a surface under test comprising:
  1. a light source which produces and projects alone a projection axis monochromatic light at each of two wavelengths $\lambda_1$ and $\lambda_2$ selected according to the specific OVM of interest;
  2. means for locating the surface under test to receive the light with the projection axis at a specific angle to the surface;
  3. two photodetectors, the first of which is located to receive light reflected at a first scattering angle $\varnothing_1$, and the second of which is located so as to receive light reflected at a second scattering angle $\varnothing_2$, from the surface, each photodetector producing an analogue signal indicative of the intensity of light incident thereon;
  4. means for amplifying the signals from the photodetectors;
  5. means for computing the value of the magnitude of the difference between the amplified intensity values for $\lambda_1$ light reflected/scattered from the surface at $\varnothing_1$ and $\varnothing_2$ less the difference between the amplified intensity values for $\lambda_2$ light at $\varnothing_1$ and $\varnothing_2$;
  6. means for generating an output signal dependent on the magnitude of the computed difference value to indicate the presence of the material on the surface, and further comprising comparison means for generating a YES/NO signal indicating if the particular OVM is present if the computed difference value is greater than a predetermined value obtained using a test sample surface having a known concentration of the OVM therein or thereon.

32. Apparatus by which an output signal is generated indicative of the presence of a specific OVM in or on a surface under test comprising:
  1. a light source which produces and projects along a projection axis monochromatic light at each of two wavelengths $\lambda_1$ and $\lambda_2$ selected according to the specific OVM of interest;
  2. means for locating the surface under test to receive the light with the projection axis at a specific angle to the surface;
  3. two photodetectors, the first of which is located to receive light reflected at a first scattering angle $\varnothing_1$, and the second of which is located so as to receive light reflected at a second scattering angle $\varnothing_2$, from the surface, each photodetector producing an analogue signal indicative of the intensity of light incident thereon;
  4. means for amplifying the signals from the photodetectors;
  5. means for computing the value of the magnitude of the difference between the amplified intensity values for $\lambda_1$ light reflected/scattered from the surface at $\varnothing_1$ and $\varnothing_2$ less the difference between the amplified intensity values for $\lambda_2$ light at $\varnothing_1$ and $\varnothing_2$;
  6. means for generating an output signal dependent on the magnitude of the computed difference value to indicate the presence of the material on the surface, and further comprising memory means having stored therein a range of possible values for the computed difference magnitude corresponding to different concentrations per unit area of the specific OVM of interest in or on the surface and comparator means whereby the computed difference magnitude for an unknown surface is compared with the range of values in the memory means to determine the best match and from a look-up table the concentration of the OVM on the surface.

33. A method of determining if a surface contains a specific material comprising the steps of:
  (1) illuminating the surface using light containing two substantially monochromatic components of wavelength $\lambda_1$ and $\lambda_2$
  (2) detecting the intensity of the light reflected or scattered by the surface at first, second and third angles $\varnothing_1$, $\varnothing_2$ and $\varnothing_3$, such that $\varnothing_1$ corresponds to back scattered light, $\varnothing_2$ corresponds to a near specular reflection, and $\varnothing_3$ corresponds to light leaving the surface at a glancing scattering angle,
  (3) generating three output signals by computing hue ratios $h_{\varnothing 1}$, $h_{\varnothing 2}$ and $h_{A3}$, being the ratio of the pairs of intensity values from each of the three detectors for the two monochromatic $\lambda_1$ and $\lambda_2$ components of illumination, and
  (4) comparing the computed hue ratios with a predetermined group of three stored values, obtained by experiment, to generate a final output signal whose value depends on the comparison.

34. A method as claimed in claim 33 wherein the intensity values from the photo-detectors are adjusted to compensate for background light by measuring and storing the photodetector output signal value when a surface is present but no $\lambda_1$ or $\lambda_2$ illumination is incident thereon, and deducting the stored value from intensity values produced by the photodetectors when subjected to $\lambda_1$ or $\lambda_2$ reflected/scattered light.

35. A method as claimed in claim 33 wherein the angles are selected as being $\varnothing_1=45°$, $\varnothing_2=90°$ and $\varnothing_3=110°$.

36. A method as claimed in claim 35 wherein values of $\lambda_1$ and $\lambda_2$ are selected so that different groups of three hue values will arise depending on whether the coating or ink in or on a surface under test is a pearlescent OVM, a non-pearlescent OVM, or a non-OVM substance, and in the case of the latter to distinguish between matt and glossy coatings.

37. A method as claimed in claim 36 wherein two values for $\lambda_1$ and $\lambda_2$ which enable such identification to occur are: $\lambda_1=654$ nm and $\lambda_2=574$ nm.

38. A method of determining the material present in or on a surface for which three hue ratios $h_{\varnothing 1}$, $h_{\varnothing 2}$ and $h_{\varnothing 3}$ are determined using the method of claim 33 as between a matt ink, a glossy ink, an OVM ink, and a pearlescent OVM ink by checking the hue ratios against the following criteria:

(i) $h_{\varnothing1}$, $h_{\varnothing2}$ and $h_{\varnothing3}$ are substantially constant with scattering angle (indicating a matt ink), (ii) $h_{\varnothing1}$, $h_{\varnothing2}$ and $h_{\varnothing3}$ tend to unity (indicating a glossy ink), (iii) $h_{\varnothing1}$, $h_{\varnothing2}$ and $h_{\varnothing3}$ decrease with increasing scattering angle, and the decreases tend to be substantial (indicating an OVM ink), (iv) specular reflection comprises a saturation colour and the $h_{\varnothing2}$ ratio diverges from unity (indicating a pearlescent OVM ink).

39. A method as claimed in claim 33 in which the angle of incidence of the illuminating light on the surface is at or near 45°.

40. A method as claimed in claim 39 wherein the illuminating light is collimated.

41. Apparatus adapted to perform the method of claim 33, comprising:
(1) a light source which produces and projects along a projection axis monochromatic light at each of two wavelengths $\lambda_1$ and $\lambda_2$,
(2) platform means for locating a surface under test thereon to receive the light, with the projection axis at a specific angle to the surface,
(3) three photo-detectors located relative to the platform so as to separately receive reflected/scattered light from a surface thereon at three different angles $\varnothing_1$, $\varnothing_2$, and $\varnothing_3$, where $\varnothing_1$ corresponds to back scattered light, $\varnothing_2$ to near specular reflection and $\varnothing_3$ to light leaving the surface at a shallow angle (a glancing scattering angle),
(4) means for amplifying the signals from the photo-detectors,
(5) means for computing the ratio of the response of each photo-detector to the two different wavelengths in the reflected/scattered light incident thereon after taking background light into account,
(6) comparator means for comparing the three ratio values so obtained with at least one set of three stored values, and generating an output signal dependent on the comparison.

42. Apparatus as claimed in claim 41 wherein the photo-detector output signals are adjusted for background illumination before the hue ratios are computed.

43. Apparatus as claimed in claim 42 wherein background intensity level signal values are obtained by noting each photo-detector output signal value with the surface in place but when no $\lambda_1$ or $\lambda_2$ illumination is present, and means is provided for storing the background intensity level output signals.

44. Apparatus as claimed in claim 42 further comprising computing means whereby the stored value is deducted from subsequent output signals from each photo-detector obtained signal value when the surface is illuminated by $\lambda_1$ and $\lambda_2$ illumination.

45. Apparatus as claimed in claim 41 in which the detectors, light source and computing means are electronically hard wired.

46. Apparatus as claimed in claim 41 wherein the illuminating and detecting means are hard wired and supply signals to, and are controlled by, a computer with a suitable interface and data acquisition card.

47. Apparatus as claimed in claim 41 further comprising analogue signal amplifying means for amplifying intensity signals from the photo-detectors.

48. Apparatus as claimed in claim 47 further comprising analogue to digital converter (ADC) means adapted to convert the amplified signals to digital signals for computation by the computing means and/or storage.

49. Apparatus as claimed in claim 41 wherein the comparator means generates either a YES/NO signal in response to the comparison depending on whether or not the three computed values are similar to three stored values, or an identification signal indicating which of a plurality of groups of stored values (each comprising a group of three such values) the three computed values most closely correspond.

50. A method of identifying the presence of a particular type of material on a printed or coated surface, comprising the steps of:
1. illuminating the surface at a pre-set angle to the surface with substantially monochromatic light at three wavelengths $\lambda_1$, $\lambda_2$ and $\lambda_3$ selected in accordance with the particular type of material,
2. detecting light reflected from the surface at three different angles $\varnothing_1$, $\varnothing_2$ and $\varnothing_3$, one of which $\varnothing_2$ corresponds to near specular reflection and the other two of which are selected in accordance with the particular type of material and are at or near to those at which the illumination wavelengths give good reflectance changes for the particular type of material,
3. computing three hue values from the intensity values determined by each detector for each of the three monochromatic illumination components $\lambda_1$, $\lambda_2$ and $\lambda_3$ respectively, thereby to produce nine hue values relating to the surface,
4. comparing the nine hue values so obtained with a stored group of nine hue values, obtained by performing the method on a surface containing a particular concentration of the particular type of material, and
5. generating a final output signal whose value depends on the comparison.

51. A method as claimed in claim 50 wherein the hue values are computed after taking into account and adjusting the photo-detector output signals for any background illumination.

52. A method as claimed in claim 51 wherein the outputs are corrected for background illumination by noting the photo-detector output signals with the surface present but in the absence of any $\lambda_1$, $\lambda_2$ or $\lambda_3$ illumination, and storing the output signals for each of the three detectors for deduction from the output signal values for the respective detectors when the surface is illuminated by the $\lambda_1$, $\lambda_2$ and $\lambda_3$ illuminations.

53. A method as claimed in claim 50 wherein the final output signal is a binary signal and has one value only if identity or near identity is obtained by the comparison, thereby indicating that the particular type of material is present.

54. A method as claimed in claim 50 wherein the comparison is performed by calculating the nearest neighbour classifier using the nine stored hue values for the particular material.

55. A method as claimed in claim 54 wherein the nearest neighbour classifier is computed by summing the squares of the differences between the computed hue values and stored hue values and comparing the sum with a threshold, wherein in the case of identity the value of the sum is zero and near identity situations are identified if the magnitude of the sum is less than a small numerical value selected for the threshold.

56. A method as claimed in claim 50 wherein computation of the nine hue values $r_{\varphi1}$ $g_{\varphi1}$ etc., for the three detectors receiving reflected/scattered light at the angles $\varnothing_1$ and $\varnothing_2$ and $\varnothing_3$ at the wavelengths $\lambda_1$, $\lambda_2$ and $\lambda_3$, each of which produces an intensity value in the detector output of $R_{\varphi1}$, $G_{\varphi1}$, $B_{\varphi1}$, $R_{\varphi2}$, $G_{\varphi2}$, $B_{\varphi2}$, $R_{\varphi3}$, $G_{\varphi3}$, and $B_{\varphi3}$ respectively, and where the background illumination produces an intensity value $D_{\phi 1}$, $D_{\phi 2}$ etc., in the detector output, is achieved by using the equations.

$$r_{\phi 1}=(R_{\phi 1}-D_{\phi 1})/(R_{\phi 1}+G_{\phi 1}+B_{\phi 1}-3D_{\phi 1})$$

$$g_{\phi 1}=(G_{\phi 1}-D_{\phi 1})/(R_{\phi 1}+G_{\phi 1}+B_{\phi 1}-3D_{\phi 1})$$

$$b_{\phi 1}=(B_{\phi 1}-D_{\phi 1})/(R_{\phi 1}+G_{\phi 1}+B_{\phi 1}-3D_{\phi 1})$$

$$r_{\phi 2}=(R_{\phi 2}-D_{\phi 2})/(R_{\phi 2}+G_{\phi 2}+B_{\phi 2}-3D_{\phi 2})$$

$$g_{\phi 2}=(G_{\phi 2}-D_{\phi 2})/(R_{\phi 2}+G_{\phi 2}+B_{\phi 2}-3D_{\phi 2})$$

$$b_{\phi 2}=(B_{\phi 2}-D_{\phi 2})/(R_{\phi 2}+G_{\phi 2}+B_{\phi 2}-3D_{\phi 2})$$

$$r_{\phi 3}=(R_{\phi 3}-D_{\phi 3})/(R_{\phi 3}+G_{\phi 3}+B_{\phi 3}-3D_{\phi 3})$$

$$g_{\phi 3}=(G_{\phi 3}-D_{\phi 3})/(R_{\phi 3}+G_{\phi 3}+B_{\phi 3}-3D_{\phi 3})$$

$$b_{\phi 3}=(B_{\phi 3}-D_{\phi 3})/(R_{\phi 3}+G_{\phi 3}+B_{\phi 3}-3D_{\phi 3})$$

where $R_{\phi 1,2,3}$ are the $\lambda_1$ illuminated intensity signals from detectors at scattering angles of $\emptyset_1$, $\emptyset_2$, and $\emptyset_3$ respectively; $G_{\phi 1,2,3}$ and $B_{\phi 1,2,3}$ are the same but for $\lambda_2$ and $\lambda_3$ illumination respectively.

57. A method of calibrating apparatus comprising the steps of performing the method of claim 56 using a surface containing a given concentration of the particular material of interest and computing the 9 values $r_{\phi 1}$, $g_{\phi 1}$ etc., and storing the computed values as $\alpha_1$, $\alpha_2$, $\alpha_3$, $\beta_1$, $\beta_2$, $\beta_3$, $\gamma_1$, $\gamma_2$, $\gamma_3$.

58. A method as claimed in claim 57 wherein the method is repeated and the results stored for each of a plurality of surfaces containing different known inks/coatings.

59. A method of computing a nearest neighbour value E using values obtained from the equations $$r_{\phi 1}=(R_{\phi 1}-D_{\phi 1})/(R_{\phi 1}+G_{\phi 1}+B_{\phi 1}-3D_{\phi 1})$$

$$g_{\phi 1}=(G_{\phi 1}-D_{\phi 1})/(R_{\phi 1}+G_{\phi 1}+B_{\phi 1}-3D_{\phi 1})$$

$$b_{\phi 1}=(B_{\phi 1}-D_{\phi 1})/(R_{\phi 1}+G_{\phi 1}+B_{\phi 1}-3D_{\phi 1})$$

$$r_{\phi 2}=(R_{\phi 2}-D_{\phi 2})/(R_{\phi 2}+G_{\phi 2}+B_{\phi 2}-3D_{\phi 2})$$

$$g_{\phi 2}=(G_{\phi 2}-D_{\phi 2})/(R_{\phi 2}+G_{\phi 2}+B_{\phi 2}-3D_{\phi 2})$$

$$b_{\phi 2}=(B_{\phi 2}-D_{\phi 2})/(R_{\phi 2}+G_{\phi 2}+B_{\phi 2}-3D_{\phi 2})$$

$$r_{\phi 3}=(R_{\phi 3}-D_{\phi 3})/(R_{\phi 3}+G_{\phi 3}+B_{\phi 3}-3D_{\phi 3})$$

$$g_{\phi 3}=(G_{\phi 3}-D_{\phi 3})/(R_{\phi 3}+G_{\phi 3}+B_{\phi 3}-3D_{\phi 3})$$

$$b_{\phi 3}=(B_{\phi 3}-D_{\phi 3})/(R_{\phi 3}+G_{\phi 3}+B_{\phi 3}-3D_{\phi 3})$$

where $R_{\phi 1,2,3}$ are the $\lambda_1$ illuminated intensity signals from detectors at scattering angles of $\emptyset_1$, $\emptyset_2$, and $\emptyset_3$ respectively; $G_{\phi 1,2,3}$ and $B_{\phi 1,2,3}$ are the same but for $\lambda_2$ and $\lambda_3$ illumination respectively,
and values stored using the results of the method of claim 58 by using the equation:

$$E = (r_{\phi 1}-\alpha_1)^2 + (g_{\phi 1}-\beta_1)^2 + (b_{\phi 1}-\gamma_1)^2 +$$
$$(r_{\phi 2}-\alpha_2)^2 + (g_{\phi 2}-\beta_2)^2 + (b_{\phi 2}-\gamma_2)^2 +$$
$$(r_{\phi 3}-\alpha_3)^2 + (g_{\phi 3}-\beta_3)^2 + (b_{\phi 3}-\gamma_3)^2.$$

60. A method of determining if a particular material is present in or on a surface under test comprising the step of computing E by the method of claim 59 and noting the value of E.

61. A method of determining which of a plurality of possible materials exist in or on a surface comprising pre-storing different groups of $\alpha$, $\beta$, $\gamma$ values for different pre-measured samples and performing nearest neighbour threshold classification using each of the stored $\alpha$, $\beta$, $\gamma$ value sets, in the equation of claim 59, until the lowest value of the sum is obtained, indicating the best match, and generating an output signal indicative of the material characteristic of the group of $\alpha$, $\beta$, $\gamma$ values so identified.

62. Apparatus adapted to perform the method of claim 60 comprising:
  (1) three monochromatic light sources producing light of $\lambda_1$ $\lambda_2$ and $\lambda_3$ wavelengths, the particular wavelengths being selected in relation to the material to be identified,
  (2) means for projecting the light at a particular angle towards a support means on which a sheet of material the surface of which is to be investigated can be laid, the angle being selected in relation to the material to be identified,
  (3) three photo-detectors arranged relative to the support means to receive reflected/scattered light along three different directions therefrom, the directions being selected in relation to the material to be identified;
  (4) computing means adapted to receive intensity signals from the three detectors and compute therefrom nine hue values corresponding to ratios of intensity signal values and combinations of such signal values, from each detector;
  (5) memory means adapted to store at least one set of nine hue values obtained by using a sheet of material containing at least in or on the surface thereof the material which is to be looked for in other surfaces,
  (6) comparison means for comparing computed and stored hue values to generate an output signal depending on the comparison.

63. Apparatus as claimed in claim 62 wherein the hue values are computed after taking into account and adjusting the photo-detector output signals for, any background illumination.

64. Apparatus as claimed in claim 62 wherein the comparison means comprises a computing means adapted to compute the sum of the squares of the differences between the computed and stored hue values.

65. Apparatus as claimed in claim 62 wherein the projection angle is 45°.

66. Apparatus as claimed in claim 62 further comprising collimating means to collimate the projected light.

67. Apparatus as claimed in claim 62 wherein each photo-detector comprises a photo-diode.

68. Apparatus as claimed in claim 67 wherein lens means is provided for focusing reflected/scattered light from the surface onto each photo-diode.

69. Apparatus as claimed in claim 68 wherein the lens means has an aperture which is selected so as to limit the angular range of scattered light which will reach its associated photo-detector.

70. Apparatus as claimed in claim 62 wherein each of the monochromatic light sources is an LED.

71. Apparatus as claimed in claim 62 which includes a pulsed power supply for the LED's, such that the three LED's are operated alternately in series, with an off period to allow background light to be measured.

72. Apparatus as claimed in claim 71 wherein the repetition rate of the LED's 1 KHz.

73. Apparatus as claimed in claim 71 wherein the repetition rate is less than 1 MHz.

74. A method of determining the presence of a particular material especially an OVM on or in a surface comprising performing any two of the methods of determining if a surface contains a specific OVM comprising the steps of:
(1) illuminating the surface using light containing two substantially monochromatic components of wavelength $\lambda_1$ and $\lambda_2$,
(2) detecting the intensity of scattered light from the surface at two scattering angles $\emptyset_1$ and $\emptyset_2$ selected according to the OVM of interest,
(3) computing the magnitude of the difference between the intensity values for $\lambda_1$ light at $\emptyset_1$ and $\emptyset_2$ less the difference between the intensity values for $\lambda_2$ light at $\emptyset_1$ and $\emptyset_2$, and
(4) generating an output signal indicating the presence or absence of the specific OVM depending on the computed difference magnitude relative to a predetermined value,
on the surface and noting the results obtained from the two methods, and generating a final output signal indicating the material is in or on the surface depending on the results obtained from the two methods, wherein the two methods are performed in parallel so that the results obtained by performing the two methods are available at substantially the same point in time to enable a final classification signal to be produced.

75. A method of determining the presence of a particular material especially an OVM on or in a surface comprising performing any two of the methods of determining if a surface contains a specific OVM comprising the steps of:
(1) illuminating the surface using light containing two substantially monochromatic components of wavelength $\lambda_1$ and $\lambda_2$,
(2) detecting the intensity of scattered light from the surface at two scattering angles $\emptyset_1$ and $\emptyset_2$ selected according to the OVM of interest,
(3) computing the magnitude of the difference between the intensity values for $\lambda_1$ light at $\emptyset_1$ and $\emptyset_2$ less the difference between the intensity values for $\lambda_2$ light at $\emptyset_1$ and $\emptyset_2$, and
(4) generating an output signal indicating the presence or absence of the specific OVM depending on the computed difference magnitude relative to a predetermined value,
on the surface and noting the results obtained from the two methods, and generating a final output signal indicating the material is in or on the surface depending on the results obtained from the two methods, wherein the two methods are performed one after the other in quick succession, and the result(s) of the first method to be performed is/are stored for combining with the result(s) from the second method to be performed, to produce the final classification signal.

76. A method of article authentication wherein genuine articles are coated over at least part of their surface with a known OVM comprising the steps of:
(1) illuminating the surface using light containing two substantially monochromatic components of wavelength $\lambda_1$ and $\lambda_2$,
(2) detecting the intensity of scattered light from the surface at two scattering angles $\emptyset_1$ and $\emptyset_2$ selected according to the OVM of interest,
(3) computing the magnitude of the difference between the intensity values for $\lambda_1$ light at $\emptyset_1$ and $\emptyset_2$ less the difference between the intensity values for $\lambda_2$ light at $\emptyset_1$ and $\emptyset_2$, and
(4) generating an output signal indicating the presence or absence of the specific OVM depending on the computed difference magnitude relative to a predetermined value,
and selecting the scattering and photo-detector angles and the wavelengths of the illuminating light in accordance with the OVM which should be on the article, and comparing the output signal value produced by the method against a look-up table (having at least one value therein) to generate an authentication or rejection signal depending on the value of the output signal.

77. A method as claimed in claim 76 wherein the article comprises a passport, an ID card, a driving licence, a banknote, a bond, a share certificate, a postage stamp or any other security document.

78. A method as claimed in claim 76 wherein only part of the surface carries the OVM and the area of the spot of light formed thereon by the illuminating light is no larger than the said area.

79. A method as claimed in claim 78 wherein at least the said area of the surface is maintained flat and at an appropriate angle to the illuminating light beam.

80. A method of checking the quality of the printing or coating of at least part of a substrate surface so as to deposit a particular OVM thereon, comprising the step of illuminating the part of the surface which has been printed or coated with the OVM and investigating the reflected light in accordance with a method as claimed in claim 1 and generating a pass or fail signal depending on the value of the output signal generated by the method.

81. A method as claimed in claim 80 wherein the printed substrate is sheet material which has been or is being, or will be printed, to form one or more security documents.

82. A method as claimed in claim 81 wherein the security documents are banknotes and the OVM is applied to some or all of the surface of the sheet material before, during or after it is printed to create the banknotes.

83. A method as claimed in either of claim 81 wherein the sheet material is moving relative to the LED and photodiode detector assembly at a linear speed of the order of 20 meters per second.

84. A printing or coating apparatus adapted to apply a specific OVM to sheet material in combination with apparatus as claimed in claims 18 adapted to generate a pass or fail signal depending on the value of the output signal produced by the apparatus as printed or coated sheet material moves relative thereto.

85. A document sorting apparatus by which documents can be sorted according to whether or not a particular OVM is present in the surface of each document in combination with apparatus as claimed in claim 18 adapted to generate a first control signal if the value of the output signal generated by the apparatus for a specific document indicates the particular OVM is present therein and a second control signal if the output signal indicates no OVM to be present, and supplying a route controlling signal to the routeing apparatus to route the specific document to one of two destinations depending on whether a first or second control signal is generated by the apparatus.

86. A method of detecting the presence of a non-pearlescent OVM in or on a surface, comprising the steps of illuminating the surface at a first angle to the surface and detecting and determining the frequency spectrum of scattered light in two different directions from the surface, one direction subtending an angle to the surface at a second angle which is substantially different from the said first angle and is substantially parallel to the plane of the surface, and the other direction subtending an angle to the surface at a third angle which is substantially closer to the said first angle than the said one direction, and in which the angle of the one direction to the surface at the second angle is in the range 1° to 15° and the angle made by the other direction to the surface at the third angle is within 10° of the said first angle.

87. A method as claimed in claim 86, wherein the said second angle is 10° and the third angle equals the said first angle.

88. A method of determining the presence of a pearlescent OVM in or on a surface comprising the steps of illuminating the surface at a first angle and firstly detecting and determining the frequency spectrum of substantially direct specular reflection from the surface, and secondly detecting and determining the frequency spectrum of scattered light leaving the surface at an angle which is different from that at which direct specular reflection occurs, wherein the second detection is of forwardly scattered light, and wherein the forwardly scattered light is detected at an angle to the said surface which is in the range 1° to 15°.

89. A method as claimed in claim 88, wherein the angle is 10°.

90. A method as claimed in claim 88, wherein the second detection is of back scattered light.

91. A method as claimed in claim 90, wherein the back scattered light is detected at an angle within 10° of the direction in which illuminating light is projected towards the surface.

92. A method as claimed in claim 91 wherein the back scattered light is detected at substantially the same angle as that which the illuminating light makes to the said surface.

93. A method as claimed in claim 86, wherein the two detections are performed simultaneously.

94. A method as claimed in claim 86, wherein the two detections are performed in succession one after the other.

95. A method as claimed in claim 94, wherein a single detector is employed, which is moved between the two positions to allow light which is being reflected from or scattered by the surface in the different directions of interest to be intercepted.

96. A method as claimed in claim 86, wherein a plurality of detectors is provided each fixed in position to intercept reflected or scattered light as appropriate, and the detectors are separately interrogated either one after the other, to provide a succession of intensity values, or simultaneously to provide a corresponding plurality of intensity values.

97. A method as claimed in claim 86, wherein the spectral determination of the light incident on the or each detector is performed by the detector by choice of a suitable photosensitive element or a combination of one or more filters and at least one photo-detector which will supply different signals or different values of a parameter of a signal, depending on the wavelength of light incident thereon.

98. A method as claimed in claim 97, wherein the illuminating light is white light.

99. A method as claimed in claim 86, wherein the illuminating light is made up of two or more distinct monochromatic components having different (known) wavelengths.

100. A method of article authentication wherein genuine articles are coated over at least part of their surface with a known OVM, comprising the steps of:

1. illuminating the surface at a pre-set angle to the surface with substantially monochromatic light at three wavelengths $\lambda_1$, $\lambda_2$ and $\lambda_3$ selected in accordance with the particular type of material,
2. detecting light reflected from the surface at three different angles $\varnothing_1$, $\varnothing_2$ and $\varnothing_3$, one of which $\varnothing_2$ corresponds to near specular reflection and the other two of which are selected in accordance with the particular type of material and are at or near to those at which the illumination wavelengths give good reflectance changes for the particular type of material,
3. computing three hue values from the intensity values determined by each detector for each of the three monochromatic illumination components $\lambda_1$, $\lambda_2$ and $\lambda_3$ respectively, thereby to produce nine hue values relating to the surface,
4. comparing the nine hue values so obtained with a stored group of nine hue values, obtained by performing the method on a surface containing a particular concentration of the particular type of material, and
5. generating a final output signal whose value depends on the comparison, and selecting the scattering and photo-detector angles and the wavelengths of the illuminating light in accordance with the OVM which should be on the article, and comparing the output signal value produced by the method against a look-up table (having at least one value therein) to generate an authentication or rejection signal depending on the value of the output signal.

101. A method as claimed in claim 100 wherein the article comprises a passport, an ID card, a driving licence, a banknote, a bond, a share certificate, a postage stamp or any other security document.

102. A method as claimed in claim 100 wherein only part of the surface carries the OVM and the area of the spot of light formed thereon by the illuminating light is no larger than the said area.

103. A method as claimed in claim 102 wherein at least the said area of the surface is maintained flat and at an appropriate angle to the illuminating light beam.

104. A method of checking the quality of the printing or coating of at least part of a substrate surface so as to deposit a particular OVM thereon, comprising the step of illuminating part of the surface which has been printed or coated with the OVM and investigating reflected light in accordance with a method comprising the steps of:

1. illuminating the surface at a pre-set angle to the surface with substantially monochromatic light at three wavelengths $\lambda_1$, $\lambda_2$ and $\lambda_3$ selected in accordance with the particular type of material,
2. detecting light reflected from the surface at three different angles $\varnothing_1$, $\varnothing_2$, and $\varnothing_3$, one of which $\varnothing_2$ corresponds to near specular reflection and the other two of which are selected in accordance with the particular type of material and are at or near to those at which the illumination wavelengths give good reflectance changes for the particular type of material,
3. computing three hue values from the intensity values determined by each detector for each of the three monochromatic illumination components $\lambda_1$, $\lambda_2$ and $\lambda_3$ respectively, thereby to produce nine hue values relating to the surface,
4. comparing the nine hue values so obtained with a stored group of nine hue values, obtained by performing the method on a surface containing a particular concentration of the particular type of material, and 5. generating a final output signal whose value depends on the comparison, and generating a pass or fail signal depending on the value of the output signal generated by the method.

105. A method as claimed in claim 104 wherein the printed substrate is sheet material which has been or is being, or will be printed, to form one or more security documents.

106. A method as claimed in claim 105 wherein the security documents are banknotes and the OVM is applied to some or all of the surface of the sheet material before, during or after it is printed to create the banknotes.

107. A method as claimed in either of claim 105 wherein the sheet material is moving relative to the LED and photodiode detector assembly at a linear speed of the order of 20 meters per second.

* * * * *